(12) United States Patent
Matthews et al.

(10) Patent No.: US 11,116,416 B2
(45) Date of Patent: Sep. 14, 2021

(54) PORTABLE HEART MOTION MONITOR

(71) Applicants: Cardiac Motion, LLC, Truckee, CA (US); The Regents of The University of California, Oakland, CA (US)

(72) Inventors: Dennis Matthews, Truckee, CA (US); Xiaoguang Liu, Davis, CA (US); Songjie Bi, Davis, CA (US)

(73) Assignees: Cardiac Motion, LLC, Truckee, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 14/736,745

(22) Filed: Jun. 11, 2015

(65) Prior Publication Data

US 2015/0359463 A1 Dec. 17, 2015

Related U.S. Application Data

(60) Provisional application No. 62/145,649, filed on Apr. 10, 2015, provisional application No. 62/010,653, filed on Jun. 11, 2014.

(51) Int. Cl.
*A61B 5/00* (2006.01)
*A61B 5/0507* (2021.01)
*A61B 5/024* (2006.01)
*A61B 5/361* (2021.01)

(52) U.S. Cl.
CPC ............ *A61B 5/0507* (2013.01); *A61B 5/024* (2013.01); *A61B 5/7282* (2013.01); *A61B 5/0022* (2013.01); *A61B 5/361* (2021.01)

(58) Field of Classification Search
CPC . A61B 5/1102; A61B 5/02028; A61B 5/6823; A61B 5/7282
See application file for complete search history.

(56) References Cited

U.S. PATENT DOCUMENTS

| 5,274,271 A | 12/1993 | McEwan et al. |
| 5,292,348 A | 3/1994 | Saumarez et al. |
| 5,511,553 A | 4/1996 | Segalowitz |
| 5,573,012 A | 11/1996 | McEwan |
| 5,738,102 A | 4/1998 | Lemelson |

(Continued)

FOREIGN PATENT DOCUMENTS

| CN | 202669497 U | 1/2013 |
| EP | 2368492 A1 | 9/2011 |

(Continued)

OTHER PUBLICATIONS

International search report and written opinion dated Nov. 4, 2015 for PCT Application No. US2015/035405.

(Continued)

*Primary Examiner* — Joseph M Santos Rodriguez
(74) *Attorney, Agent, or Firm* — Wilson Sonsini Goodrich & Rosati

(57) ABSTRACT

The present disclosure describes a method and device to monitor the heart of a subject using radio signals. Availability of a portable heart monitor that can be used in a subject's home can increase patient compliance and improve diagnosis rates of cardiac conditions. A mobile heart monitor can be especially useful to those subjects who are elderly, incapacitated, or do not have easy access to a clinic, doctor's office, or hospital.

32 Claims, 21 Drawing Sheets

(56) References Cited

U.S. PATENT DOCUMENTS

| | | | |
|---|---|---|---|
| 5,766,208 | A | 6/1998 | McEwan |
| 6,681,404 | B1 | 1/2004 | Adlard et al. |
| 8,068,051 | B1 | 11/2011 | Osterweil |
| 8,378,879 | B2 | 2/2013 | Lewis et al. |
| 8,463,361 | B2 | 6/2013 | Tupin, Jr. |
| 8,494,615 | B2 | 7/2013 | Melamed et al. |
| 8,502,729 | B2 | 8/2013 | Leach, Jr. et al. |
| 8,562,526 | B2 | 10/2013 | Heneghan et al. |
| 2002/0147408 | A1* | 10/2002 | Chen ............... A61N 1/3962 600/513 |
| 2004/0015087 | A1 | 1/2004 | Boric-Lubecke et al. |
| 2005/0052322 | A1 | 3/2005 | Park et al. |
| 2005/0073424 | A1 | 4/2005 | Ruoss et al. |
| 2005/0100376 | A1 | 5/2005 | Omotani |
| 2006/0094937 | A1 | 5/2006 | Immoreev et al. |
| 2008/0294019 | A1 | 11/2008 | Tran |
| 2009/0048500 | A1 | 2/2009 | Corn |
| 2009/0203972 | A1 | 8/2009 | Heneghan et al. |
| 2009/0227882 | A1 | 9/2009 | Foo |
| 2009/0278728 | A1 | 11/2009 | Morgan et al. |
| 2010/0152600 | A1 | 6/2010 | Droitcour et al. |
| 2010/0179421 | A1* | 7/2010 | Tupin ............... A61B 5/026 600/426 |
| 2010/0179438 | A1 | 7/2010 | Heneghan et al. |
| 2010/0240999 | A1* | 9/2010 | Droitcour ........... A61B 5/05 600/453 |
| 2010/0245091 | A1 | 9/2010 | Singh et al. |
| 2011/0218586 | A1 | 9/2011 | Li |
| 2012/0101398 | A1* | 4/2012 | Ramanathan ....... A61B 5/044 600/523 |
| 2013/0053653 | A1 | 2/2013 | Cuddihy et al. |
| 2013/0135137 | A1* | 5/2013 | Mulder ............. A61B 5/0507 342/28 |
| 2013/0274623 | A1* | 10/2013 | Zhang ............. A61B 5/04012 600/517 |
| 2013/0281800 | A1 | 10/2013 | Saroka et al. |

FOREIGN PATENT DOCUMENTS

| | | |
|---|---|---|
| WO | WO 2004/109316 A2 | 12/2004 |
| WO | WO 2007/101343 A1 | 9/2007 |
| WO | WO 2007/124126 A2 | 11/2007 |
| WO | WO 2007/143535 A2 | 12/2007 |
| WO | WO-2008026157 A2 | 3/2008 |
| WO | WO 2008/057883 A2 | 5/2008 |
| WO | WO 2008/148040 A1 | 12/2008 |
| WO | WO-2007052108 A3 | 4/2009 |
| WO | WO 2011/146517 A2 | 11/2011 |
| WO | WO 2012/148280 A1 | 11/2012 |
| WO | WO 2013/118121 A1 | 8/2013 |

OTHER PUBLICATIONS

Azevedo, et al. Micropower impulse radar. Science and Technology Review. Jan./Feb. 1996; 16-29.

European Search Report and Search Opinion dated Jan. 8, 2018 for European Patent Application No. EP15806524.3.

Oyvind et al. Detecting changes in the human heartbeat with on-body radar. Radar Conference (Radar), 2013 IEEE. DOI: 10.1109/RADAR.2013.6586027.

Examination Report dated Aug. 20, 2019 for Australian Application No. 2015274528.

Office Action dated Jun. 4, 2019 for Japanese Application No. 2017-517214.

Brovoll et al. Optimal frequency range for medical radar measurements of human Heartbeats using body-contact radar. 2013 35th Annual International Conference of the IEEE Engineering in Medicine and Biology Society (EMBC), Osaka, 2013, pp. 1752-1755.

Fletcher et al. Wearable Doppler Radar with Integrated Antenna for Patient Vital Sign Monitoring. RSW (2010) pp. 276-279.

Zito et al. Feasibility Study and Design of a Wearable System-on-a-Chip Pulse Radar for Contactless Cardiopulmonary Monitoring. International Journal of Telemedicine and Applications, vol. 2008, Article ID 328597, 10 pages.

\* cited by examiner

Panel A.

Panel B.

Panel A.

Panel B.

Panel C.

PORTABLE HEART MOTION MONITOR

CROSS-REFERENCE TO RELATED APPLICATIONS

This application claims the benefit of priority to U.S. Provisional Patent Application Ser. No. 62/010,653, filed on Jun. 11, 2014 and U.S. Provisional Patent Application Ser. No. 62/145,649, filed on Apr. 10, 2015, each of which is hereby incorporated by reference in its entirety.

STATEMENT REGARDING FEDERALLY SPONSORED RESEARCH OR DEVELOPMENT

The invention was made with the support of the United States government under the Small Business Technology Transfer Award 1449060 by the National Science Foundation. The government may have certain rights in the invention.

BACKGROUND

The development of cardiac testing and monitoring devices that can be used in the home has the potential to reduce healthcare costs, increase patient compliance, and improve the quality of life of patients. The elderly, incapacitated, and those without easy access to healthcare facilities can greatly benefit from home testing devices. However, current home testing devices are often uncomfortable, difficult to use, and expensive. Several challenges still exist in the creation of cost-effective, simple-to-use, and accurate home testing.

SUMMARY OF THE INVENTION

In some embodiments, the invention provides a method of detecting an irregular heartbeat in a subject, the method comprising: a) transmitting a wavelength of electromagnetic radiation to the heart of the subject; b) detecting an electromagnetic signal reflected off the heart of the subject; and c) determining based on the electromagnetic signal reflected off the heart of the subject whether the subject has an irregular heartbeat.

In some embodiments, the invention provides a method comprising: a) receiving by a computer system data associated with an electromagnetic signal reflected off a heart of a subject; b) comparing by a processor of the computer system the data associated with the electromagnetic signal reflected off the heart of the subject to a reference; c) determining based on the comparison of the data associated with the electromagnetic signal reflected off the heart of the subject to the reference whether the subject has an irregular heartbeat; and d) outputting a result of the determination.

In some embodiments, the invention provides a device comprising: a) an antenna configured to transmit electromagnetic radiation into a thoracic cavity of a subject; b) a receiver configured to detect an electromagnetic signal reflected off the subject's heart; and c) a processor configured to identify an irregular heartbeat in the subject based on the detected electromagnetic signal reflected off the subject's heart.

In some embodiments, the invention provides a device comprising: a) an antenna configured to transmit electromagnetic radiation into a thoracic cavity of a subject; b) a receiver configured to detect an electromagnetic signal reflected off the subject's heart; and c) a transmitter configured to transmit data associated with the received electromagnetic signal reflected off the subject's heart.

In some embodiments, the invention provides a method comprising: a) administering to a subject having an irregular heartbeat an intervention for the irregular heartbeat; b) monitoring the subject with a radar device; and c) determining based on the monitoring whether the intervention for the irregular heartbeat modulates the irregular heartbeat in the subject.

In some embodiments, the invention provides a method comprising: a) administering to a subject an intervention; b) monitoring the subject with a radar device; and c) determining based on the monitoring whether the intervention induces an irregular heartbeat in the subject.

DETAILED DESCRIPTION

Figure 1:
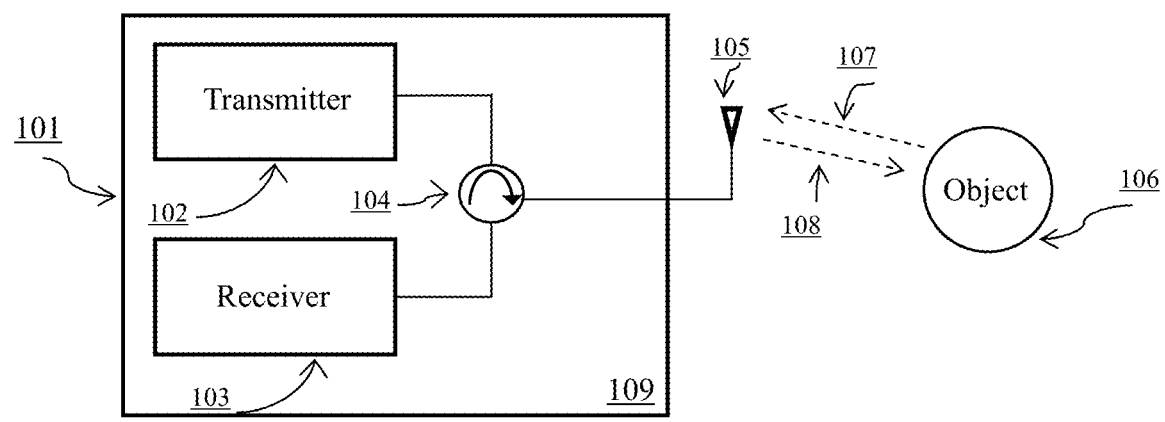
FIG. 1 depicts a representative device of the invention.

Portable testing devices have the potential to reduce healthcare costs and improve the delivery of healthcare to patients who do not have immediate or easy access to healthcare facilities. A portable heart motion monitor can rapidly and conveniently determine the cardiac status of patients without requiring travel to a hospital or doctor's office. This convenience can reduce costs by reducing frequency of hospital visits and improving diagnosis rates due to increased patient compliance. A compact and portable heart motion monitor provides a special benefit to patients who are elderly, incapacitated, or living in remote areas, who would otherwise have to travel tediously to receive adequate healthcare. The invention described herein provides a simple, cost-effective, and efficient method to obtain information about a patient's heart from anywhere that the patient goes, even in the comfort of the patient's home.

Described herein are methods and devices to measure an irregular heartbeat in a subject. A mobile device of the invention can be used in a subject's home without clinical intervention. The device described herein can detect heart motion in a subject continuously and non-invasively. The device can be worn by the subject, attached to the subject, mounted, stationary, or otherwise convenient for outpatient use.

An irregular heartbeat, also known as cardiac dysrhythmia or arrhythmia, is any of a group of conditions wherein the electrical activity of the heart is irregular and often faster or slower than is normal. An irregular heartbeat can be symptomatic of deeper underlying cardiac conditions. The standard diagnostic test for arrhythmias is electrocardiography (ECG). An ECG is a recording of the electrical activity of the heart, the output of which is a series of waveforms corresponding to the electrical impulses generated by the polarization and depolarization of cardiac tissue, known as an electrocardiogram (also ECG). While an ECG is a powerful method to glean a variety of information about a patient's cardiac status, the test requires a significant amount of clinical expertise and a visit to the clinic or hospital. This inconvenience makes the process of obtaining an ECG unappealing, especially if the patient is elderly, incapacitated, or resides in a rural area where access to a clinic can be difficult.

Device.

Diagnosis of an irregular heartbeat can be essential in determining underlying cardiac abnormalities or disease. Subjects with atrial fibrillation, for example, can have a higher risk of stroke due to the pooling of blood in atria, which can lead to blood clots. Thus, development of devices that can rapidly and easily monitor cardiac activity can lead to efficient and effective diagnoses of cardiac conditions. Devices that can be used remotely can increase patient compliance, thereby improving diagnosis success rates.

A device described herein can be worn by a subject to monitor cardiac activity in various environments. Activity can be monitored in a care setting, such as a clinic, hospital, or doctor's office, or in a place away from a clinic or a hospital, for example, at home, at school, or any place where the user wishes to wear the device. A device described herein can also be used during everyday activity, for example, while driving a car, doing daily errands, exercising, shopping, or during periods of rest or sleep. The device described herein can use, for example, electromagnetic signals to determine the motion of a subject's heart to monitor and diagnose the heart for irregularities.

A device described herein can be used during short-term visits to a clinic, hospital, or doctor's office. The device can also be used by a subject during an inpatient visit to a hospital, or while a subject is recovering in a hospital, but needs the freedom to be ambulatory.

FIG. 1 illustrates a device 101 to determine the motion of the heart of a subject. The transmitter 102 of the transceiver circuit 109 generates a signal that is routed to an antenna 105 via the duplexer 104. The signal can then propagate 108 from the antenna to an object of interest 106, such as a heart of portion thereof. The signal can be, for example, pulsed or continuous. In some embodiments, the signal is electromagnetic radiation such as a radio wave, an electromagnetic signal, a wavelength or frequency of the electromagnetic spectrum, a wavelength of light, or a photon. After transmission of the signal, the signal can be reflected 107 off the object of interest 106, such as the heart. The signal is detected by the antenna 105 and routed to the receiver 103 via the duplexer 104. In some embodiments, the device comprises a radar system. Non-limiting examples of the types of radar that can be used in the device include ultrawide bandwidth radar, continuous wave Doppler radar, pulsed Doppler radar, frequency-modulated continuous wave radar, or pseudorandom code modulated continuous wave radar.

Figure 12:
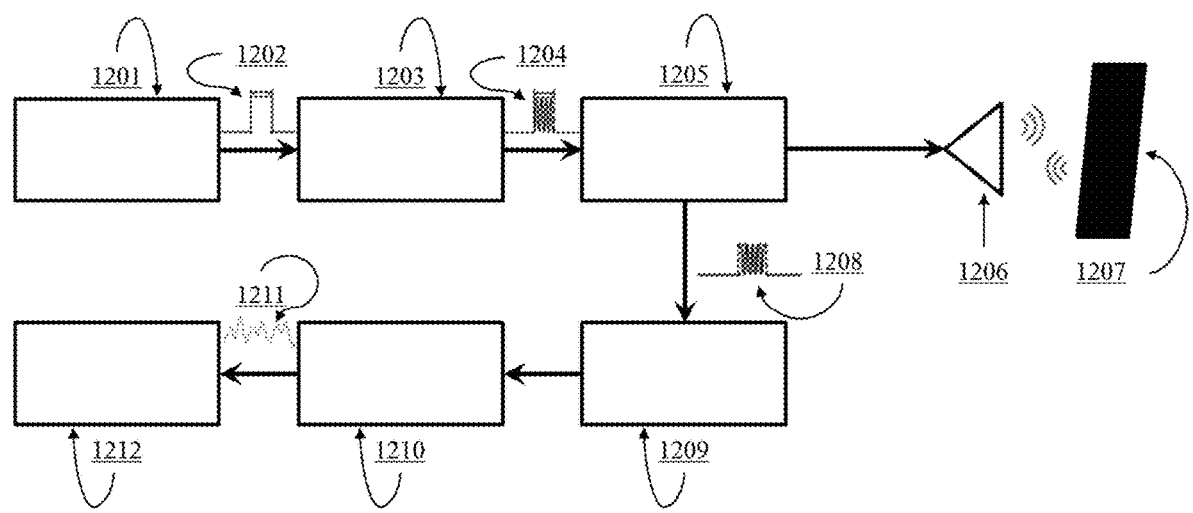
FIG. 12 depicts a representative device of the invention.

FIG. 12 illustrates an embodiment of a device to determine the motion of the heart of a subject. The pulse generator 1201 generates a pulse 1202 that is routed through a pulsed sine wave generator 1203 to generate a pulse waveform 1204. The pulse waveform 1204 is then routed to the antenna 1206 via the duplexer 1205. The pulse waveform 1204 can then propagate from the antenna 1206 to a target 1207, such as a heart of portion thereof. In some embodiments, the pulse waveform 1204 is electromagnetic radiation such as a radio wave, an electromagnetic signal, a wavelength or frequency of the electromagnetic spectrum, a wavelength of light, or a photon. After transmission of the pulse waveform 1204, the pulse waveform 1204 can be reflected off the target 1207, such as the heart. The pulse waveform 1204 is detected by the antenna 1206 and routed to the mixer 1209 via the duplexer 1205, which converts the detected pulse waveform into a duplexed waveform 1208. The duplexed waveform 1208 is propagated from the mixer 1209 to the amplifier and filters 1210 to generate the filtered waveform 1211. The filtered waveform 1211 is then propagated to the signal processing and display unit 1212. In some embodiments, the device comprises a radar system. Non-limiting examples of the types of radar that can be used in the device include ultrawide bandwidth radar, continuous wave Doppler radar, pulsed Doppler radar, frequency-modulated continuous wave radar, and pseudorandom code modulated continuous wave radar.

In some embodiments, multiple radar sensors can be used to increase the accuracy of the cardiac measurements. Multiple radar sensors also measure heart motion profiles from different positions of view and generate a multi-dimensional data set that can be inverted to solve for the motion of the heart in two dimensions. This method can provide accurate measurements by reducing the effect of random movement or misalignment of individual radar sensors.

Figure 13:
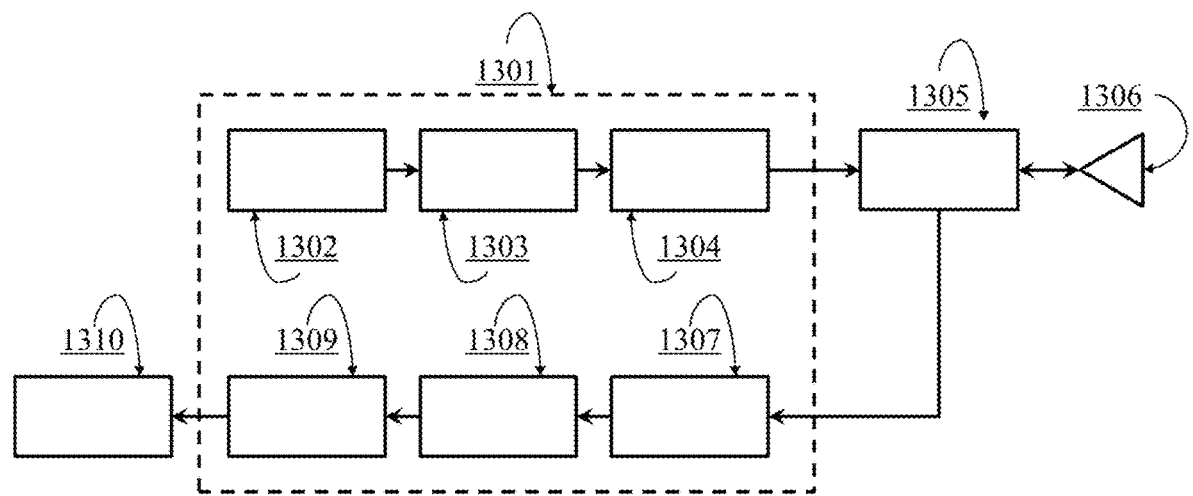
FIG. 13 depicts a representative device of the invention.

FIG. 13 illustrates an embodiment of a device to determine the motion of the heart of a subject. Within a printed circuit board 1301, a voltage controlled oscillator 1302 generates a waveform. The waveform is then propagated through a splitter 1303 and a first amplifier 1304 to the circulator 1305. The waveform is then carried from a circulator 1305 to an antenna 1306. A reflected waveform is then carried from the antenna 1306 to the circulator 1305. The waveform is then propagated to a second amplifier 1307. The waveform is then filtered through a bandpass filter 1308. The filtered waveform is then decoded using a quadrature demodulation chip 1309. The decoded waveform is then transmitted to a signal acquisition unit 1310. In some embodiments, the device comprises a radar system. Non-limiting examples of the types of radar that can be used in the device include ultrawide bandwidth radar, continuous wave Doppler radar, pulsed Doppler radar, frequency-modulated continuous wave radar, and pseudorandom code modulated continuous wave radar.

In some embodiments, a device described herein comprises a monostatic radar architecture, wherein only one antenna is used for both transmission and reception. In some embodiments, a device described herein comprises a duplexer, which can separate transmitted and received signals when one antenna is used for both transmission and reception. In a monostatic radar system, signals generated are passed directly to the antenna, while received signals from the antenna are routed to the receiver portion. A duplexer can provide isolation between the transmit and receive paths, allowing for one antenna to perform both functions.

In some embodiments, a device described herein comprises a bistatic radar architecture. In a device comprising a bistatic radar architecture, two antennas are spatially separated for the transmit and receive paths.

Non-limiting examples of antennae that can be used in the device include an isotropic radiator, a dipole antenna, a Yagi-Uda antenna, a random wire antenna, a horn antenna, a parabolic antenna, and a patch antenna. In some embodiments, the antenna can be detachable or removable from the device. In some embodiments, the antenna can be interchangeable or exchangeable for a different antenna, for example, an antenna of a differing strength. The antenna can be placed, for example, inside, outside, in proximity to, adjacent to, on top of, or below the device.

In some embodiments, the device can determine if the subject has a condition associated with an irregular heartbeat. Non-limiting examples of conditions associated with an irregular heartbeat include paroxysmal atrial fibrillation, paroxysmal atrial flutter, atrial fibrillation, atrial flutter, ventricular fibrillation, ventricular flutter, supraventricular tachycardia, Wolff-Parkinson-White syndrome, premature ventricular contraction, premature atrial contraction, sick sinus syndrome, sinus arrhythmia, sinus tachycardia, multifocal atrial tachycardia, or bradycardia.

A device can comprise a computer system that can receive data associated with a signal reflecting off the subject's heart. The data that is received by the computer system can then be compared by a processor of the computer system to a reference to determine if the subject has an irregular heartbeat. Non-limiting examples of references that can be used by the computer system include past measurements from the subject, measurements from a healthy subject, statistical averages of the symptom being measured, and reference texts. The computer system can then output a result of the determination. In some embodiments, the processor is located in a housing common to the source of the signal in the device. In some embodiments, the processor is not located in a housing common to the source of the signal in the device.

In some embodiments, the device comprises a processor coupled to a transmitter configured to transmit data from the device to a remote location, for example, a hospital, a clinic, or a doctor's office. The transmitter can be configured to transmit data wirelessly, for example, via Bluetooth, wireless networks, cell phone networks, a cloud network, or the internet. For example, the device can use Bluetooth to connect to an analysis device, including but not limited to, a cell phone or computer system. In some embodiments, the transmission is wired. The processor can be configured to transmit data to a plurality of receivers in a plurality of geographic locations. In some embodiments, the processor can transmit data over a distance of about 1 mile, about 2 miles, about 3 miles, about 4 miles, about 5 miles, about 6 miles, about 7 miles, about 8 miles, about 9 miles, or about 10 miles. In some embodiments, the processor can transmit data over a distance of at least 10 miles. In some embodiments, the processor can transmit data over a distance of at least 50 miles. In some embodiments, the device comprises a Global Positioning System (GPS).

A device described herein can be, or cannot be, worn by a subject. The device can be attached to a subject's body using, for example, a chest strap, a chest vest, an arm band, a wrist band, a headband, a belt, an adhesive tape, or glue. A device described herein can be embedded in a subject's clothing, for example, an undergarment, a bra, a shirt, a jacket, or a sweater. A device described herein can be embedded in, for example, a watch, an earring, a necklace, a ring, or a bracelet. The device can also be unattached from the subject's body. A device described herein can be attached to, for example, a wall, a headboard, a bed, a mirror, a nightstand, a chair, or other furniture in proximity to the subject. The device can be embedded in, for example, a mattress, a pillow, a comforter, or a sofa.

A device described herein can be, or cannot be, at a distance from a subject. The distance between the device and the subject can be zero, at least about 1 centimeter (cm), at least about 2 cm, at least about 3 cm, at least about 4 cm, at least about 5 cm, at least about 6 cm, at least about 7 cm, at least about 8 cm, at least about 9 cm, at least about 10 cm, at least about 11 cm, at least about 12 cm, at least about 13 cm, at least about 14 cm, at least about 15 cm, at least about 16 cm, at least about 17 cm, at least about 18 cm, at least about 19 cm, at least about 20 cm, at least about 21 cm, at least about 22 cm, at least about 23 cm, at least about 24 cm, at least about 25 cm, at least about 26 cm, at least about 27 cm, at least about 28 cm, at least about 29 cm, at least about 30 cm, at least about 31, at least about 32 cm, at least about 33 cm, at least about 34 cm, at least about 35 cm, at least about 36 cm, at least about 37 cm, at least about 38 cm, at least about 39 cm, at least about 40 cm, at least about 41 cm, at least about 42 cm, at least about 43 cm, at least about 44 cm, at least about 45 cm, at least about 46 cm, at least about 47 cm, at least about 48 cm, at least about 49 cm, at least about 50 cm, at least about 60 cm, at least about 70 cm, at least about 80 cm, at least about 90 cm, at least about 1 meter (m), at least about 2 m, at least about 3 m, at least about 4 m, at least about 5 m, at least about 6 m, at least about 7 m, at least about 8 m, at least about 9 m, at least about 10 m, at least about 15 m, or at least about 20 m.

The distance between the device and the subject can be at most about 1 centimeter (cm), at most about 2 cm, at most about 3 cm, at most about 4 cm, at most about 5 cm, at most about 6 cm, at most about 7 cm, at most about 8 cm, at most about 9 cm, at most about 10 cm, at most about 11 cm, at most about 12 cm, at most about 13 cm, at most about 14 cm, at most about 15 cm, at most about 16 cm, at most about 17 cm, at most about 18 cm, at most about 19 cm, at most about 20 cm, at most about 21 cm, at most about 22 cm, at most about 23 cm, at most about 24 cm, at most about 25 cm, at most about 26 cm, at most about 27 cm, at most about 28 cm, at most about 29 cm, at most about 30 cm, at most about 31, at most about 32 cm, at most about 33 cm, at most about 34 cm, at most about 35 cm, at most about 36 cm, at most about 37 cm, at most about 38 cm, at most about 39 cm, at most about 40 cm, at most about 41 cm, at most about 42 cm, at most about 43 cm, at most about 44 cm, at most about 45 cm, at most about 46 cm, at most about 47 cm, at most about 48 cm, at most about 49 cm, at most about 50 cm, at most about 60 cm, at most about 70 cm, at most about 80 cm, at most about 90 cm, at most about 1 meter (m), at most about 2 m, at most about 3 m, at most about 4 m, at most about 5 m, at most about 6 m, at most about 7 m, at most about 8 m, at most about 9 m, at most about 10 m, at most about 15 m, or at most about 20 m.

A device described herein can be, or cannot be, in contact with a subject's skin. The device can be placed in proximity to, for example, the chest, the sternum, the heart, or the thoracic cavity of a subject. The device can be placed directly on, for example, the chest, the sternum, or the thoracic cavity of a subject. In some embodiments, the device can be placed in the center of the chest, the upper part of the chest, the lower part of the chest, the left part of the center of the chest, or the right part of the center of the chest of a subject. In some embodiments, the device can be placed on the back of a subject, for example, in line with, above, below, left, or right of the sternum. In some embodiments, the device can be placed in front of, for example, the chest, the sternum, or the thoracic cavity of a subject.

A device described herein can be used by a subject holding breath. In some embodiments, the device can be used by a subject breathing normally.

A device described herein can be used by a subject hourly, daily, weekly, monthly, yearly, occasionally, frequently, continuously, or chronically. A device described herein can be used by a subject as needed based on a condition of the subject, upon a doctor's recommendation, as desired by the subject, as required to monitor the condition of the subject properly, or for diagnostic or research purposes.

In some embodiments, a device of the invention has an average output power of about 1 µW, about 2 µW, about 3 µW, about 4 µW, about 5 µW, about 6 µW, about 7 µW, about 8 µW, about 9 µW, about 10 µW, about 20 µW, about 30 µW, about 40 µW, about 50 µW, about 60 µW, about 70 µW, about 80 µW, about 90 µW, about 100 µW, about 200 µW, about 300 µW, about 400 µW, about 500 µW, about 600 µW, about 700 µW, about 800 µW, about 900 µW, about 1 mW, about 2 mW, about 3 mW, about 4 mW, about 5 mW, about 6 mW, about 7 mW, about 8 mW, about 9 mW, about 10 mW, about 15 mW, about 20 mW, about 25 mW, about 30 mW, about 35 mW, about 40 mW, about 45 mW, about 50 mW, about 60 mW, about 70 mW, about 80 mW, about 90 mW, or about 100 mW.

A device described herein can produce pulses of electromagnetic waves. The duration of the pulses can be about 1 ps, about 2 ps, about 3 ps, about 4 ps, about 5 ps, about 6 ps, about 7 ps, about 8 ps, about 9 ps, about 10 ps, about 20 ps, about 30 ps, about 40 ps, about 50 ps, about 60 ps, about 70 ps, about 80 ps, about 90 ps, about 100 ps, about 110 ps, about 120 ps, about 130 ps, about 140 ps, about 150 ps, about 160 ps, about 170 ps, about 180 ps, about 190 ps, about 200 ps, about 250 ps, about 300 ps, about 350 ps, about 400 ps, about 450 ps, about 500 ps, about 600 ps, about 700 ps, about 800 ps, about 900 ps, about 1 ns, about 2 ns, about 3 ns, about 4 ns, about 5 ns, about 6 ns, about 7 ns, about 8 ns, about 9 ns, about 10 ns, about 20 ns, about 30 ns, about 40 ns, about 50 ns, about 60 ns, about 70 ns, about 80 ns, about 90 ns, about 100 ns, about 200 ns, about 300 ns, about 400 ns, about 500 ns, about 600 ns, about 700 ns, about 800 ns, about 900 ns, or about 1 µs. The repetition rate of the pulses can be about 0.1 MHz, about 0.2 MHz, about 0.3 MHz, about 0.4 MHz, about 0.5 MHz, about 0.6 MHz, about 0.7 MHz, about 0.8 MHz, about 0.9 MHz, about 1 MHz, about 2 MHz, about 3 MHz, about 4 MHz, about 5 MHz, about 6 MHz, about 7 MHz, about 8 MHz, about 9 MHz, about 10 MHz, about 15 MHz, about 20 MHz, about 25 MHz, about 30 MHz, about 35 MHz, about 40 MHz, about 45 MHz, about 50 MHz, about 60 MHz, about 70 MHz, about 80 MHz, about 90 MHz, or about 100 MHz.

Non-limiting examples of device shape include a cube, a sphere, a cylinder, a square, a rectangle, and a circle. A device described herein can have a height (H), width (W), and depth (D), each independently of about 0.05 inches, about 0.1 inches, about 0.15 inches, about 0.2 inches, about 0.25 inches, about 0.3 inches, about 0.35 inches, about 0.4 inches, about 0.45 inches, about 0.5 inches, about 0.6 inches, about 0.7 inches, about 0.8 inches, about 0.9 inches, or about 1 inch. In some embodiments, the device is a cube. In some embodiments, the device can have dimensions of about 1 inch height by about 1 inch width by about 0.2 inches depth.

Non-limiting examples of materials that can be used in the manufacture of the device include polyvinyl chloride, polyethylene, polypropylene, polystyrene, polyurethane, polyethylene terephthalate, polycarbonate, silicone, and combinations thereof. Further non-limiting examples of materials that can be used in the manufacture of the device include steel, low-carbon steel, medium-carbon steel, high-carbon steel, aluminum, brass, copper, lead, magnesium, nickel, titanium, zinc, and combinations thereof. Additional non-limiting examples of materials that can be used in the manufacture of the device include copper wire, aluminum wire, XHHW wire, THWN wire, and THHN wire.

Non-limiting examples of chips that can be used in the manufacture of the device include dynamic random access memory chips, microprocessors, application specific integrated circuits, digital signal processors, programmable memory chips, and combinations thereof.

Non-limiting examples of semiconductors that can be used in the manufacture of the device include diamond, silicon, germanium, tin, silicon carbide, selenium, tellurium, boron nitride, zinc oxide, copper (I) oxide, and combinations thereof.

In some embodiments, the device has a total mass of less than about 100 grams. The total mass of the device can be about 1 gram, about 2 grams, about 3 grams, about 4 grams, about 5 grams, about 6 grams, about 7 grams, about 8 grams, about 9 grams, about 10 grams, about 15 grams, about 20 grams, about 25 grams, about 30 grams, about 35 grams, about 40 grams, about 45 grams, about 50 grams, about 60 grams, about 70 grams, about 80 grams, about 90 grams, about 100 grams, about 110 grams, about 120 grams, about 130 grams, about 140 grams, about 150 grams, about 200 grams, about 250 grams, about 300 grams, about 350 grams, about 400 grams, about 450 grams, about 500 grams, about 550 grams, about 600 grams, about 650 grams, about 700 grams, about 750 grams, about 800 grams, about 850 grams, about 900 grams, about 950 grams, or about 1000 grams.

Any tool, interface, engine, application, program, service, command, or other executable item can be provided as a module encoded on a computer-readable medium in computer executable code. In some embodiments, the invention provides a computer-readable medium encoded therein computer-executable code that encodes a method for performing any action described herein, wherein the method comprises providing a system comprising any number of modules described herein, each module performing any function described herein to provide a result, such as an output, to a user.

Applications of a Device of the Invention.

The device described herein can be used to monitor the cardiac activity of a subject, and detect abnormalities. The monitoring can detect the motion of the subject's heart. The device can also detect, for example, the relative position of a portion of the heart as compared to the rest of the heart, a movement of the left atrium, a movement of the right atrium, a movement of the left ventricle, a movement of the right ventricle, a change in a dimension of the heart, the heart rate, the pattern of the heart rate, the regularity of the heartbeat, the irregularity of the heartbeat, the strength of the heartbeat, the intensity of the heartbeat, the position of the heart muscles, the velocity of the heart muscles, the relative strength of diastole, the relative strength of systole, the sinus rhythm of the atria, the sinus rhythm of the ventricles, ejection fraction, cardiac output, and stroke volume.

The device described herein can obtain and record measurements, for example, when the subject is at rest, in motion, doing light exercise, doing heavy exercise, walking, running, jogging, biking, or sleeping. Measurements taken during these times can be compared to readings taken during other times to determine the cardiac activity of the subject.

A subject can be, for example, an elderly adult, an adult, an adolescent, a child, a toddler, or an infant. A subject can be, for example, an individual with a heart condition or an individual without a heart condition. A subject can be a patient.

The device described herein can be used to detect an irregular heartbeat in a subject. An irregular heartbeat, also known as cardiac dysrhythmia or arrhythmia, is characterized by an abnormal heart rate or rhythm, and a change in the electrical activity of the heart. An irregular heartbeat can be caused by, for example, coronary artery disease, electrolyte imbalances, scarring of the heart muscle from a previous heart attack, cardiomyopathy, hypertension, diabetes, hyperthyroidism, stress, smoking, medication side effects (for example, chemotherapy-induced cardiotoxicity), excessive consumption of alcohol, excessive consumption of caffeine, or drug abuse. The major symptoms of an irregular heartbeat include, for example, a fluttering sensation in the chest, palpitations, chest pain, shortness of breath, slow heartbeat, shortness of breath, dizziness, and syncope.

Atrial fibrillation is a common condition associated with an irregular heartbeat, with almost half a million cases diagnosed in the United States annually. In this condition, the normal electrical impulses produced by the sinus node of the heart for a regular heartbeat are overwhelmed by rapid electrical discharges produced in the atria and adjacent parts of the pulmonary veins. These rapid and irregular abnormal discharges can exceed 350 discharges per minute, cause ineffective contractions of the atria, and reduce the ability of the atria to pump blood into the ventricles. These complications further lead to irregular ventricular contractions, causing a discrepancy in the rate of contractions in the atria and ventricles.

Figure 2:
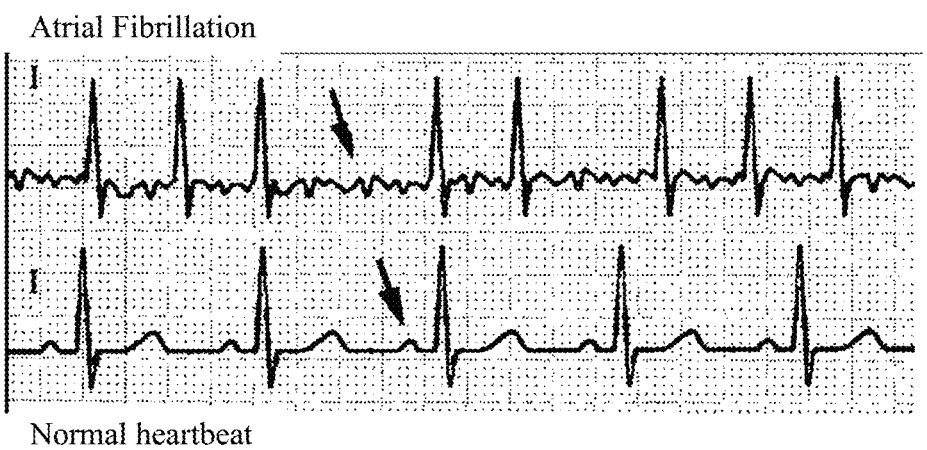
FIG. 2 shows comparative ECGs for atrial fibrillation and a normal heartbeat.

FIG. 2 shows an ECG for a subject with a normal heart rate and one for a subject with atrial fibrillation. The arrow in the bottom ECG denotes a P wave found in subjects with a normal heartbeat. The P wave on an ECG represents the depolarization that spreads through the sinoatrial node to the atria, also known as atrial depolarization. Atrial depolarization is the first step of the cardiac cycle and occurs when there is an influx of $Ca^{2+}$ ions, which leads to contractions within the atrium. A patient with atrial fibrillation will not have a P wave on an ECG due to the lack of atrial depolarization. In the place of the P wave, small spikes in electrical activity provide evidence of electrical disturbance, as denoted by the arrow in the top ECG. The major symptoms of atrial fibrillation can include palpitations, chest pain, shortness of breath, and syncope. The heart rate can exceed about 100 beats per minute. Paroxysmal atrial fibrillation can be an episode of atrial fibrillation that occurs and then stops and does not happen persistently or consistently.

Figure 3:
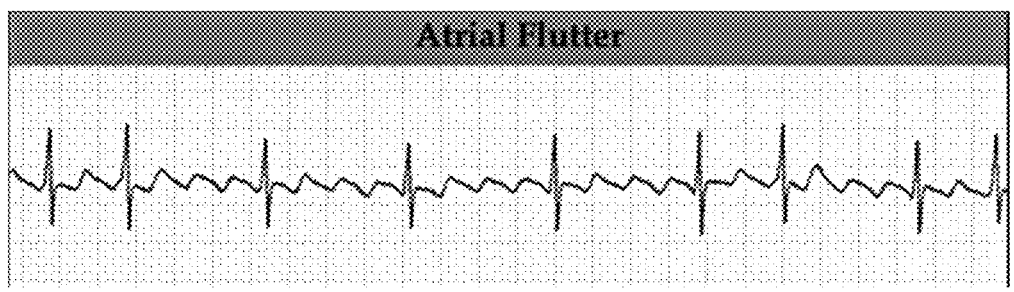
FIG. 3 is a representative ECG for atrial flutter.

Atrial flutter is an abnormal heart rhythm that occurs within the atria. Atrial flutter can be caused by a rapid electrical impulse that begins, most commonly, in the right atrium which moves in a localized self-perpetuating loop. The circuit can go around the atria at about 300 beats per minute, in turn causing the ventricles to beat very rapidly. The self-perpetuating loop circles the right atrium and passes through the cavo-tricuspid isthmus, an area of fibrous tissue in the lower atrium between the inferior vena cava and the tricuspid valve. A characteristic ECG of a patient with atrial flutter is shown in FIG. 3. The rapid, but regular, beating of the atria can lead to a saw tooth pattern on an ECG. The major symptoms of atrial flutter can include palpitations, shortness of breath, rapid heart rate, chest pain, lightheadedness, fatigue, and low blood pressure. Paroxysmal atrial flutter can be an episode of atrial flutter that occurs and then stops and does not happen persistently or consistently.

Figure 4:
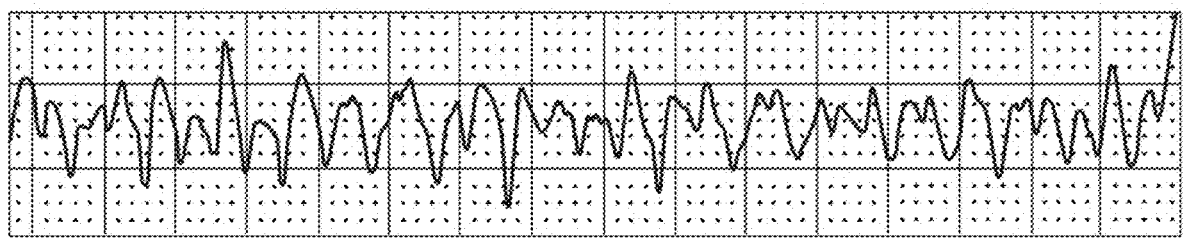
FIG. 4 is a representative ECG for ventricular fibrillation.

Ventricular flutter can be characterized by a rapid heartbeat that originates in the ventricles. Ventricular flutter generally progresses to ventricular fibrillation and is short-lived. Ventricular fibrillation can occur by an uncoordinated contraction in the ventricles, causing a quiver rather than proper contractions. The heartbeat can exceed 350 beats per minute. This improper contraction of the ventricles most often leads to cardiac arrest due to an inability of the ventricles to pump blood through the heart. The most common cause of ventricular fibrillation is coronary artery disease. The most immediate symptoms of ventricular fibrillation are sudden collapse or loss of consciousness, and fainting. Early signs of ventricular fibrillation can include dizziness, nausea, chest pain, rapid heart rate, or palpitations. Generally, if a subject is not treated within five minutes of collapse due to ventricular fibrillation, the subject will undergo cardiac arrest. The erratic heartbeats present during ventricular fibrillation can be seen in the ECG in FIG. 4.

Supraventricular tachycardia (SVT) is a rapid heart rate that originates in or above the atrioventricular node. Episodes of SVT can last for a few seconds, minutes, hours, or days. The major symptoms of SVT include a pounding heart, shortness of breath, rapid heartbeat, dizziness, chest pain, and syncope.

Wolff-Parkinson-White (WPW) syndrome is caused by the presence of an abnormal accessory electrical conduction pathway between the atria and the ventricles. Electrical signals travelling down this abnormal pathway can stimulate the ventricles to contract prematurely, resulting in a unique type of supraventricular tachycardia, referred to as an atrioventricular reciprocating tachycardia. Often, WPW syndrome is asymptomatic, but symptoms can include palpitations, shortness of breath, dizziness, and syncope.

Premature ventricular contraction (PVC) occurs when a heartbeat is initiated in the Purkinje fibers of the ventricles, rather than the sinoatrial node, where a normal heartbeat originates. PVC is a relatively common event and is generally considered benign, but can indicate hypoxia in the myocardium. PVC most commonly occurs in the elderly and in men, and is generally asymptomatic and difficult to detect without an ECG. Possible signs of a PVC event include palpitations, shortness of breath, dizziness, increased awareness of one's heartbeat, and a feeling of forceful beats.

Premature atrial contractions (PACs) occur when the heartbeat originates in the atria, rather than the sinoatrial node. PACs are a common event that can manifest in patients without underlying cardiac abnormalities, and are considered fairly benign. PACs are generally asymptomatic, but rarely present with palpitations.

Sick sinus syndrome (SSS) includes arrhythmias that originate in the sinus node. SSS is often associated with coronary artery disease and valvular lesions. SSS is most common in the elderly and in children who have undergone cardiac surgery in the atria. Symptoms of SSS include syncope, dizziness, shortness of breath, chest pain, fatigue, headache, and nausea.

Sinus arrhythmia refers to the natural variation in heartbeat that occurs with breathing. A mild slowing and acceleration of heart rate occurs with breathing. Sinus arrhythmia is most pronounced in children and steadily decreases with age.

Sinus tachycardia is a rapid heart rhythm originating in the sinoatrial node with a heartbeat that can exceed 100 beats per minute. Sinus tachycardia is generally a response to normal physiological situations such an exercise and stress. The main symptom of sinus tachycardia is an increased heart rate.

Multifocal atrial tachycardia is a cardiac arrhythmia associated with chronic obstructive pulmonary disease (COPD). Multifocal atrial tachycardia occurs when groups of cells outside of the sinoatrial node begin to control the heartbeat, and the heart rate exceeds 100 beats per minute. Symptoms can include tightness in the chest, light-headedness, syncope, palpitations, shortness of breath, and dizziness.

Bradycardia is a resting heart rate of less than 60 beats per minute, generally remaining asymptomatic until the rate drops below 50 beats per minute. Symptoms of bradycardia include fatigue, weakness, dizziness, and syncope. Bradycardia can be caused by recreational drug use, metabolic or hormonal imbalances, electrolyte imbalances, coronary artery disease, vascular heart disease, or valvular heart disease. Generally, bradycardia can be caused by problems that arise in the sinoatrial node or atrioventricular node.

A device described herein can be used to determine, observe, record, time, track, or calculate, the burden, or duration, of an irregular heartbeat in a subject. The device can record measurements for a specified period of time to determine the percentage of time the subject has an irregular heartbeat. The device can record measurements for about one minute, about 2 minutes, about 3 minutes, about 4 minutes, about 5 minutes, about 10 minutes, about 15 minutes, about 20 minutes, about 25 minutes, about 30 minutes, about 40 minutes, about 50 minutes, about one hour, about 2 hours, about 3 hours, about 4 hours, about 5 hours, about 10 hours, about 20 hours, about one day, about 2 days, about 3 days, about 4 days, about 5 days, about 6 days, about one week, about 2 weeks, about 3 weeks, about one month, about 2 months, about 3 months, about 4 months, about 5 months, about 6 months, about one year, about 2 years, or about 3 years. The burden can be determined over any time period by an analysis of the data, comparing episodes of irregular heartbeat to the subject's own ordinary heartbeat or to a reference heartbeat.

The device described herein can be used to monitor cardiac activity in a subject undergoing an intervention for an irregular heartbeat. The intervention can involve pharmacological agents, devices that are, or are not, implanted in the subject to modulate the heartbeat, surgery, and combinations thereof. The device can be used to determine if the intervention is modulating the irregular heartbeat by comparing readings taken before and after administration of the intervention, or during the course of therapy. Non-limiting examples of interventions used by a subject that can be monitored by the present invention include amiodarone, bepridil hydrochloride, disopyramide, dofetilide, dronedarone, flecainide, ibutilide, lidocaine, procainamide, propafenone, propranolol, quinidine, sotalol, tocainide, amlodipine, diltiazem, felodipine, isradipine, nicardipine, nifedipine, nimodipine, nisoldipine, verapamil, acebutolol, atenolol, betaxolol, bisoprolol, hydrochlorothiazide, carteolol, esmolol, metoprolol, nadolol, penbutolol, pindolol, timolol, warfarin, dalterparin, enoxaparin, heparin, tinzaparin, aspirin, ticlopidine, clopidogrel, dipyridamole, benazepril, captopril, enalapril, fosinopril, lisinopril, moexipril, perindopril, quinapril, ramipril, trandolapril, candesartan, eprosartan, irbesartan, losartan, temisartan, valsartan, amiloride, bumetanide, chlorothiazide, chlorthalidone, furosemide, indapamide, spironolactone, isosorbide dinitrate, nesiritide, hydralazine, minoxidil, lanoxin, atorvastatin, fluvastatin, lovastatin, pitavastatin, pravastatin, rosuvastatin, simvastatin, clofibrate, gemfibrozil, digoxin, adenosine, radiofrequency ablation, transcatheter ablation, defibrillation, a pacemaker, an implantable cardioverter defibrillator, and combinations thereof.

The device described herein can be used to monitor cardiac activity in a subject undergoing an intervention for a non-irregular heartbeat condition. The intervention can comprise pharmacological agents, surgery, and combinations thereof. The device can be used to determine whether the intervention is inducing an irregular heartbeat by comparing readings taken before and after administration of the intervention, or during the course of therapy. Non-limiting examples of interventions used by a subject that can be monitored by the present invention include diphenhydramine, chlorpheniramine, clemastine, brompheniramine, hydroxyzine, cetirizine, fexofenadine, loratadine, dextroamphetamine, methamphetamine, methylphenidate, fenfluramine, dexfenfluramine, MDMA, cocaine, pseudoephedrine, albuterol, isoproterenol, salmeterol, isoetharine, phencyclidine, tranylcypromine, phenelzine, theophylline, aminophylline, caffeine, nortriptyline, amitriptyline, imipramine, desipramine, scopolamine, propantheline, atropine, cisapride, erythromycin lactobionate, pentamidine, chloroquine, amantadine, and combinations thereof.

The device described herein can be used to monitor cardiac activity in a subject undergoing an intervention for a cancer, tumor, hyperproliferative disorder, or neoplasia. The intervention can comprise pharmacological agents, surgery, and combinations thereof. The device can be used to determine whether the intervention is inducing an irregular heartbeat by comparing readings taken before and after administration of the intervention, or during the course of therapy. Non-limiting examples of interventions used by a subject that can be monitored by the present invention include doxorubicin, adriamycin, capecitabine, gemcitabine, cytarabine, paclitaxel, docetaxel, cisplatin, carboplatin, oxaliplatin, 5-fluorouracil, chlorambucil, cyclophosphamide, busulfan, melphalan, arsenic trioxide, IL-2, methotrexate, trastuzumab, sunitinib, cetuximab, alemtuzumab, rituximab, thalidomide, amsacrine, dispeptide, and combinations thereof.

The device described herein can be used to monitor cardiac activity in a subject using recreational drugs. The device can be used to determine whether the recreational drug use is inducing an irregular heartbeat by comparing readings taken in the presence and absence of recreational drug, use, or during the course of recreational drug, use. Non-limiting examples of recreational drugs used by a subject that can be monitored by the present invention include dextroamphetamine, methamphetamine, methylphenidate, fenfluramine, dexfenfluramine, MDMA, cocaine, phencyclidine, lysergic acid diethylamide, psilocybin, morphine, heroin, volatile inhalants, *cannabis* and combinations thereof.

Signals Suitable for Use.

A detection system of the invention can comprise a transmitter, a receiver, and an antenna. The transmitter can generate a signal that is radiated into a space containing an object of interest by the antenna. The signal can then be reflected off the object of interest, and a reflected signal can be detected by the receiver. The receiver can amplify the signal for conversion to, for example, visual or audio data.

Ultrasound involves the use of high frequency sound waves outside the range of human hearing to create images of, for example, organs and systems within the human body. Medical sonography is the practice of imaging organs within the body. Ultrasound images (sonograms) are made by sending a pulse of ultrasound into tissue using an ultrasound transducer. The sound reflects and echoes off parts of the tissue and this echo is recorded and displayed as an image to the operator.

The electromagnetic (EM) spectrum is a continuum of all the possible frequencies of electromagnetic radiation. Electromagnetic radiation can be described by physical properties including frequency, wavelength, and energy. The different regions of the EM spectrum, in decreasing order of wavelength and increasing order of frequency, include radio waves, microwaves, far infrared, near infrared, visible, ultraviolet, X-rays, gamma rays, and high-energy gamma rays.

Radio waves are generally propagated via the use of an antenna and can have wavelengths that range from hundreds of kilometers to a millimeter. Radio waves can be used for communication satellites, navigation systems, radio communication, broadcasting, and radar.

Microwaves have wavelengths that range from one meter to millimeters. Microwaves are used in spacecraft communication and radar technology. Some television and telephone communications are transmitted long distances by microwaves between ground stations and communications satellites. Microwaves can be absorbed by molecules that have dipole moments in liquids.

Infrared radiation is characterized by wavelengths that range from about a millimeter to several hundred nanometers. Infrared energy is emitted or absorbed by molecules when changing rotational-vibrational movements. Infrared energy elicits vibrational modes in a molecule through a change in the dipole moment, making infrared a useful frequency range for study of these energy states for molecules. Most thermal energy emitted from objects at room temperature is infrared.

The visible region of the EM spectrum is the portion of the spectrum to which the human eye is most sensitive. Electromagnetic radiation with wavelengths of between 380 and 760 nanometers is detectable by the human eye and perceived as visible light.

Ultraviolet (UV) radiation typically has wavelengths between 100 and 400 nanometers. UV light can be found in sunlight and has the potential to damage biological molecules due to its ability to alter chemical bonds. UV rays having very short wavelengths can ionize molecules.

X-rays have wavelengths in the range of about one to tenths of a nanometer. X-rays have the ability to penetrate through relatively thick objects without much scattering or absorption, thus making them useful for imaging visually opaque objects and are widely used in medical radiography and airport security scanners.

Gamma rays have extremely short wavelengths and a very high frequency. Natural sources of gamma rays include decay from naturally occurring radioisotopes. Gamma rays are also found in space as a result of supernova explosions. Due to their high energy, gamma rays are highly penetrating and can diffuse throughout the human body and cause radiation sickness.

Radar (radio detection and ranging) is a system that can use radio waves or microwaves to determine the range, altitude, speed, and direction of objects. Radio waves are a portion of the electromagnetic spectrum and are characterized by low frequency and long wavelengths. A radar system can use radio waves as a mechanism for the detection of objects.

Ultra-wideband (UWB) radar systems can use radio waves to transmit information spread over large bandwidths, for example, greater than 500 MHz. UWB radar systems can accomplish this task via pulse-modulation of the signal, in that UWB transmissions transmit information by generating radio waves at specific time intervals over a large bandwidth. Non-UWB transmissions can employ continuous signaling in which only the frequency, power level, or phase of the wave, but not the time interval, is changed.

Doppler radar utilizes the Doppler effect to produce velocity data about objects at a distance. Doppler radar can beam a microwave signal toward a desired target and listen for a reflection. This process allows for analysis of how the object's motion alters the frequency of the returned signal motion, and provides data about the object's velocity.

Continuous wave Doppler radar transmits a continuous wave of radio energy, allowing for the determination of an object's velocity without providing any range or distance data. Frequency-modulated continuous wave (FMCW) Doppler radar differs from continuous wave Doppler radar in that the frequency of the transmitted signal can be varied, allowing for measurements of an object's distance. Use of pseudorandom code modulated continuous wave radar can provide further refinement as to an object's distance and range. This refinement occurs via modulation of the transmitter's codes to meet frequency and range requirements for the objects of interest.

Pulsed Doppler radar uses pulse-timing techniques and the Doppler effect to determine the distance of an object. Pulsed Doppler systems differ from continuous wave systems by sending short pulses of radio energy rather than a continuous transmission of radio energy to an object. The range of an object is determined by the measuring the elapsed time between pulses sent to and reflected off the object.

Figure 5:
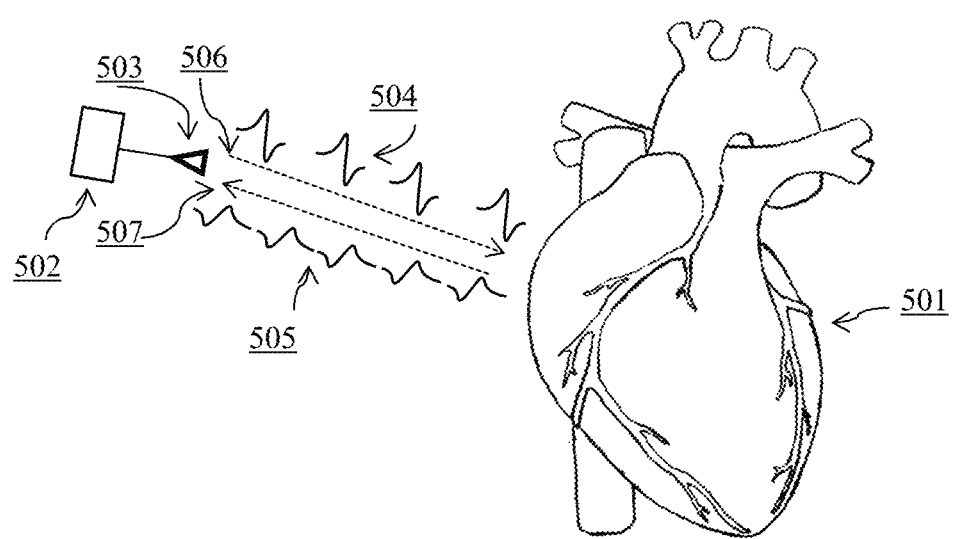
FIG. 5 depicts a function of an example device of the invention.

FIG. 5 depicts an example device of the present invention. The device 502 can comprise an antenna 503 and be positioned in proximity to, for example, a human heart 501. The antenna can transmit 506 a signal 504 to the heart. The signal 504 can reflect off, for example, the muscle tissue of the heart. The reflected signal 505 can then be received 507 by the device 502 and processed for analysis.

EXAMPLES

Example 1

Analysis of Signal Loss Inside Human Tissues

Figure 6:
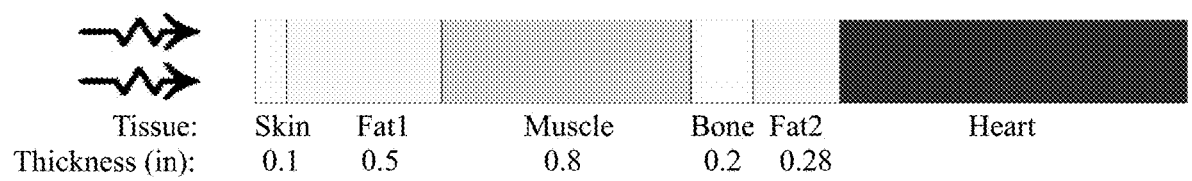
FIG. 6 illustrates the thickness of different tissues in the human body.

Performance can be optimized by positioning a device on a subject for minimal signal loss in tissue. FIG. 6 illustrates the tissue thickness, in inches, of skin, fat, muscle, and bone anterior to the heart of a human. The amount of muscle tissue is relatively low. When radar signals were radiated through various tissues including skin, fat, muscle, and bone, the greatest loss of radar signal occurred in the muscle tissue, as demonstrated in FIG. 7.

Figure 7:
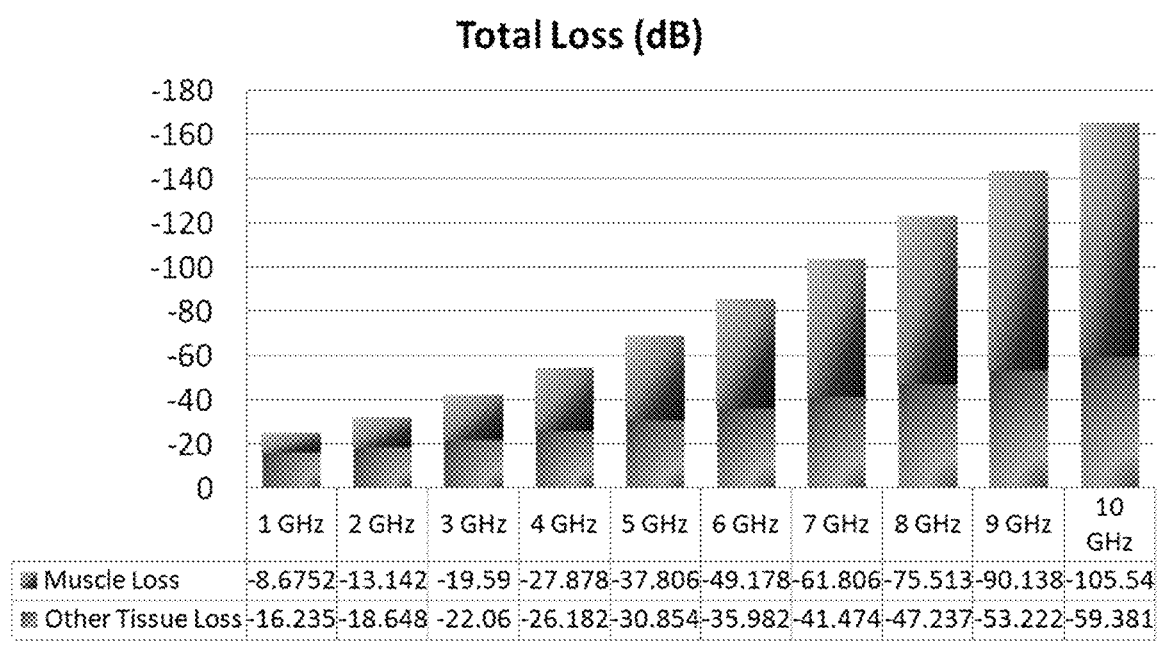
FIG. 7 depicts signal loss inside human tissue.

The loss of signal intensity was correlated positively with the frequency of the signal, as shown in FIG. 7. When the frequency (GHz) of the signal was increased, the total loss of signal (dB) was most significant in the muscle, while other tissues only accounted for a minor portion of signal loss. This analysis further indicated that the sternum, having minimal musculature, should be an effective placement for the device. This placement allows for less signal loss and dispersion.

Example 2

Modeling Methodology

To calculate the interaction of transmitted signals generated by a device described herein with heart muscles, a three-dimensional full-wave simulation was employed. In this simulation, a three-dimensional model of the heart, or chest cavity, was used. First, the complexity of the model was reduced by removing portions of the chest cavity that do not move, and thus are not relevant for modeling the motion of the heart. Next, the heart model was imported into a wave simulation program to determine the signal received at the antenna in the form of a magnetic or electric field distribution. Finally, the extracted waveforms were fed into a circuit simulator to determine the correlation between the output signal and the motion of the heart.

Example 3

Computer Architectures

Figure 8:
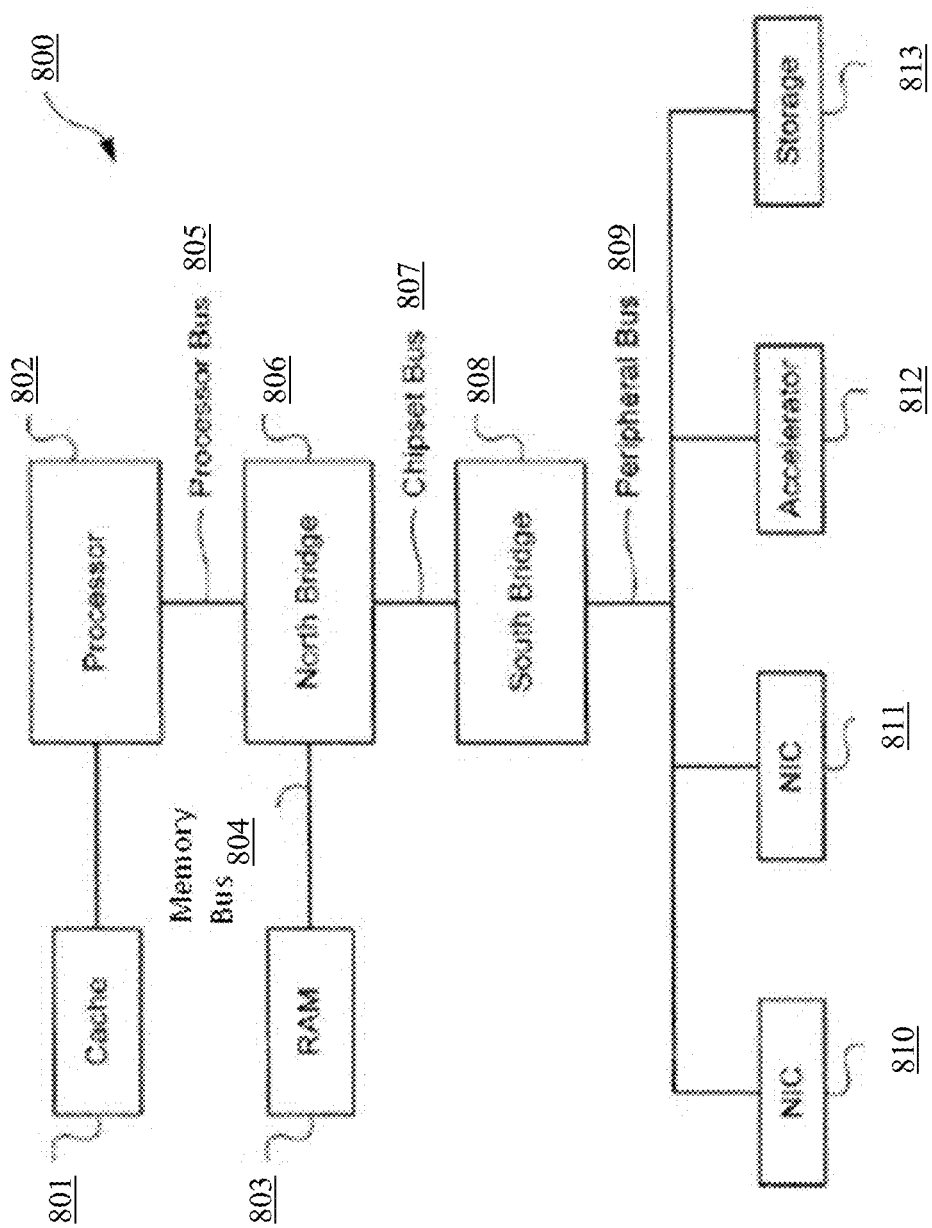
FIG. 8 is a block diagram illustrating a first example architecture of a computer system that can be used in connection with example embodiments of the present invention.

Various computer architectures are suitable for use with the invention. FIG. 8 is a block diagram illustrating a first example architecture of a computer system 800 that can be used in connection with example embodiments of the present invention. As depicted in FIG. 8, the example computer system can include a processor 802 for processing instructions. Non-limiting examples of processors include: Intel Core i7™ processor, Intel Core i5™ processor, Intel Core i3™ processor, Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can be used, whether in a single computer system, in a cluster, or distributed across systems over a network comprising a plurality of computers, cell phones, tablet computing devices, watch based devices, wrist band devices, armband devices, or personal data assistant devices.

Data Acquisition, Processing and Storage.

As illustrated in FIG. 8, a high speed cache 801 can be connected to, or incorporated in, the processor 802 to provide a high speed memory for instructions or data that have been recently, or are frequently, used by processor 802. The processor 802 is connected to a north bridge 806 by a processor bus 805. The north bridge 806 is connected to random access memory (RAM) 803 by a memory bus 804 and manages access to the RAM 803 by the processor 802. The north bridge 806 is also connected to a south bridge 808 by a chipset bus 807. The south bridge 808 is, in turn, connected to a peripheral bus 809. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 809. In some architectures, the functionality of the north bridge can be incorporated into the processor instead of using a separate north bridge chip.

In some embodiments, system 800 can include an accelerator card 812 attached to the peripheral bus 809. The accelerator can include field programmable gate arrays (FPGAs) or other hardware for accelerating certain processing.

Software Interface(s).

Software and data are stored in external storage 813 and can be loaded into RAM 803 and/or cache 801 for use by the processor. The system 800 includes an operating system for managing system resources; non-limiting examples of operating systems include: Linux, Windows™, MACOS™, BlackBerry OS™, iOS™, Android™ and other functionally-equivalent operating systems, as well as application software running on top of the operating system.

In this example, system 800 also includes network interface cards (NICs) 810 and 811 connected to the peripheral bus for providing network interfaces to external storage, such as Network Attached Storage (NAS) and other computer systems that can be used for distributed parallel processing.

Computer Systems.

Figure 9:
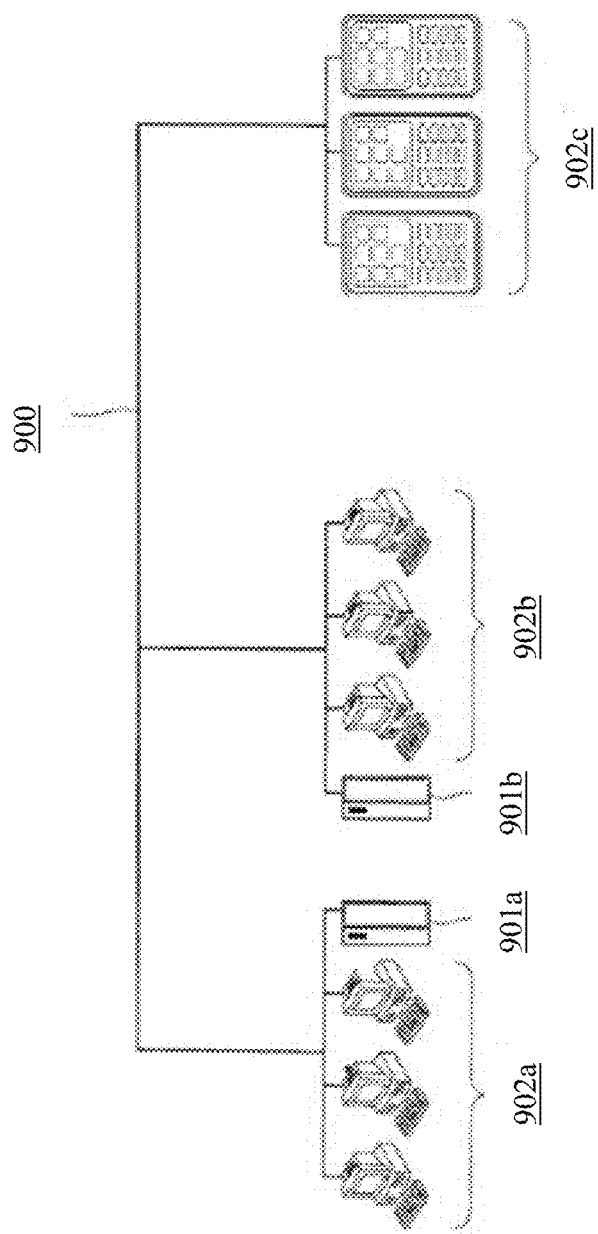
FIG. 9 is a diagram illustrating a computer network that can be used in connection with example embodiments of the present invention.

FIG. 9 is a diagram showing a network 900 with a plurality of computer systems 902a, and 902b, a plurality of cell phones and personal data assistants 902c, and Network Attached Storage (NAS) 901a, and 901b. In some embodiments, systems 902a, 902b, and 902c can manage data storage and optimize data access for data stored in Network Attached Storage (NAS) 901a and 902b. A mathematical model can be used for the data and be evaluated using distributed parallel processing across computer systems 902a, and 902b, and cell phone and personal data assistant systems 902c. Computer systems 902a, and 902b, and cell phone and personal data assistant systems 902c can also provide parallel processing for adaptive data restructuring of the data stored in Network Attached Storage (NAS) 901a and 901b. FIG. 9 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface.

In some embodiments, processors can maintain separate memory spaces and transmit data through network interfaces, back plane, or other connectors for parallel processing by other processors. In some embodiments, some or all of the processors can use a shared virtual address memory space.

Virtual Systems.

Figure 10:
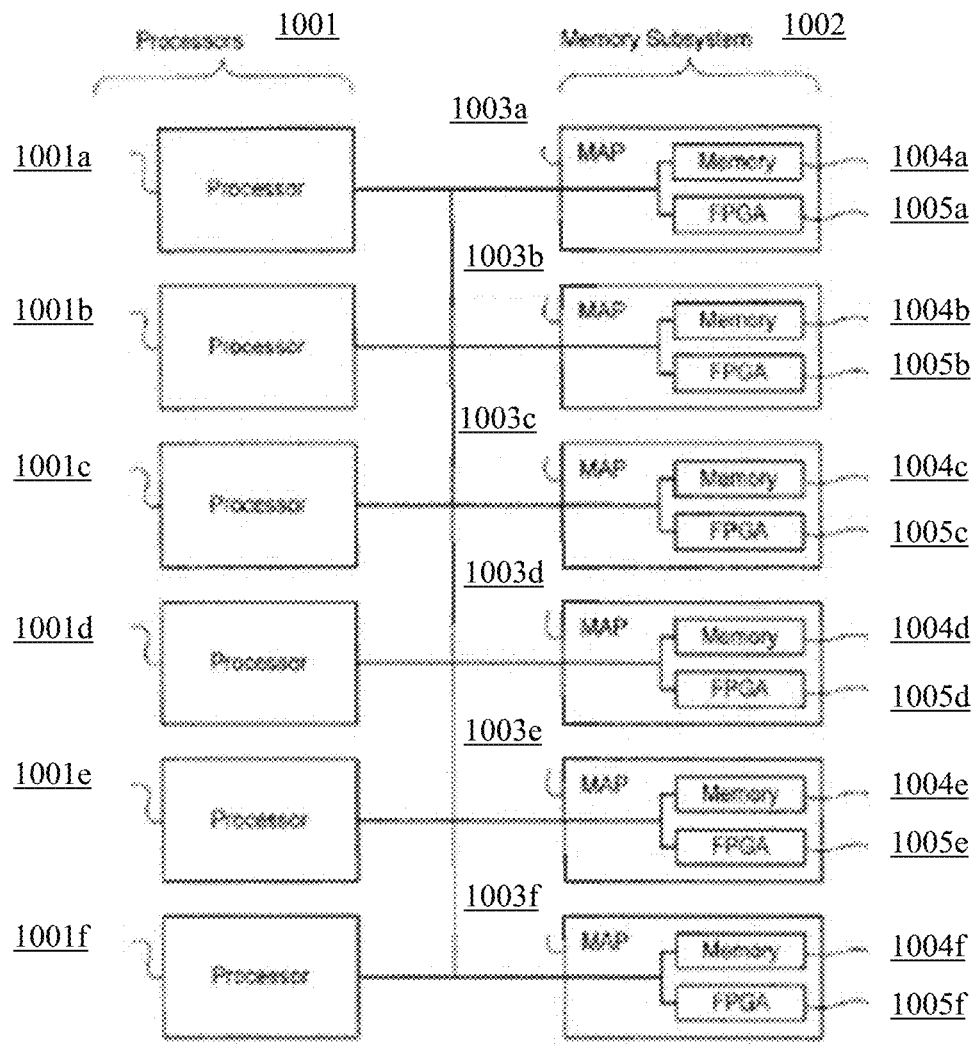
FIG. 10 is a block diagram illustrating a second example architecture of a computer system that can be used in connection with example embodiments of the present invention.

FIG. 10 is a block diagram of a multiprocessor computer system using a shared virtual address memory space. The system includes a plurality of processors 1001a-f that can access a shared memory subsystem 1002. The system incorporates a plurality of programmable hardware memory algorithm processors (MAPs) 1003a-f in the memory subsystem 1002. Each MAP 1003a-f can comprise a memory 1004*a-f* and one or more field programmable gate arrays (FPGAs) 1005*a-f*. The MAP provides a configurable functional unit and particular algorithms or portions of algorithms can be provided to the FPGAs 1005*a-f* for processing in close coordination with a respective processor. In this example, each MAP is globally accessible by all of the processors for these purposes. In one configuration, each MAP can use Direct Memory Access (DMA) to access an associated memory 1004*a-f*, allowing it to execute tasks independently of, and asynchronously from, the respective microprocessor 1001*a-f*. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 10, system on chips (SOCs), application specific integrated circuits (ASICs), or other processing and logic elements. For example, the Set Processor and Optimizer can be implemented with hardware acceleration through the use of a hardware accelerator card, such as accelerator card 812 illustrated in FIG. 8.

Figure 11:
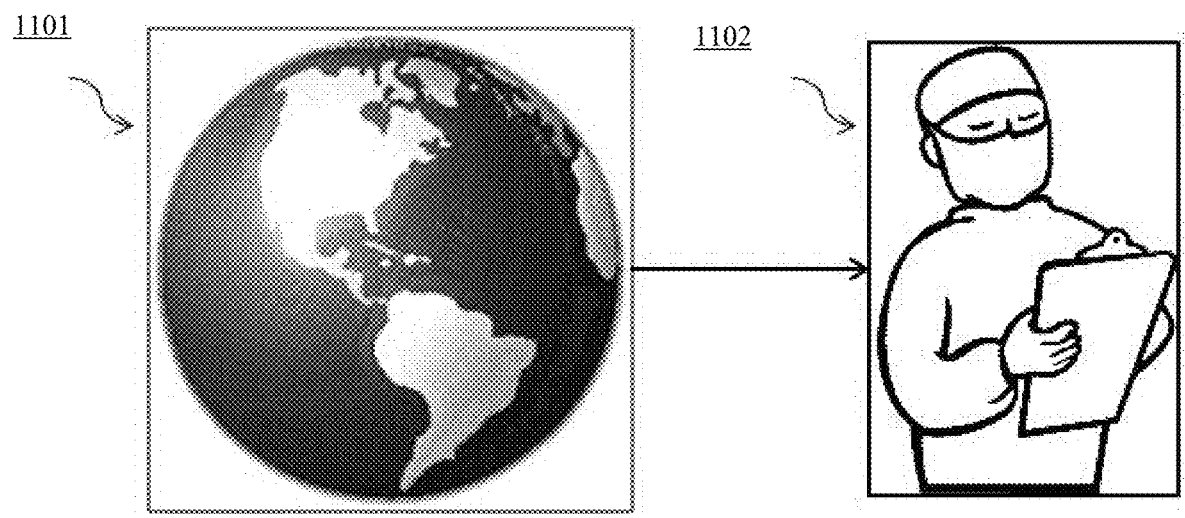
FIG. 11 illustrates a global network that can transmit a product of the invention.

Any embodiment of the invention described herein can be, for example, produced and transmitted by a user within the same geographical location. A product of the invention can be, for example, produced and/or transmitted from a geographic location in one country and a user of the invention can be present in a different country. In some embodiments, the data accessed by a system of the invention is a computer program product that can be transmitted from one of a plurality of geographic locations 1101 to a user 1102 (FIG. 11). Data generated by a computer program product of the invention can be transmitted back and forth among a plurality of geographic locations, for example, by a network, a secure network, an insecure network, an internet, or an intranet. In some embodiments, an ontological hierarchy provided by the invention is encoded on a physical and tangible product.

Any embodiment of the invention described herein can be produced and/or transmitted in an encoded form, for example, a radio frequency identification tag or barcode. In some embodiments, the data accessed by a system of the invention can be accessed from the encoded form either directly or as part of a health record. In some embodiments, the health record can be an electronic health record or digital health record. In some embodiments, the health record can be accessed by the subject or a health care provider for the subject.

Example 4

Implementations of the Device

Figure 14:
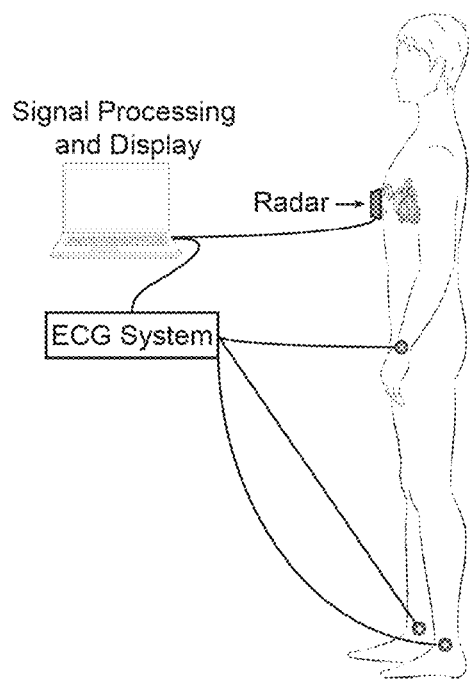
FIG. 14 illustrates representative implementations of an example device of the invention.
Figure 14:
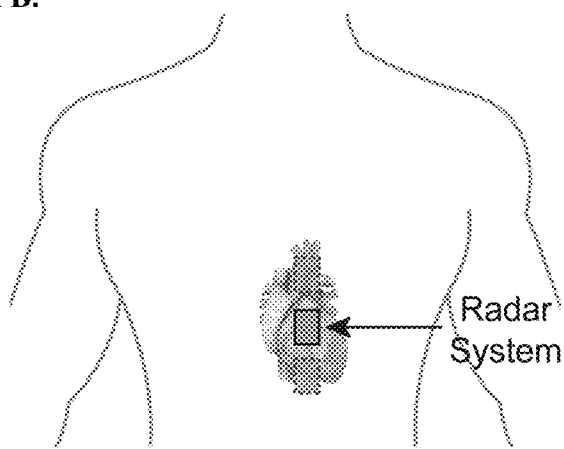

One embodiment of the invention described herein is shown in FIG. 14, panel A. A human subject stands or sits in a way that they can avoid shaking their body. The subject holds a radar device attached to their body using either their hand or a chest strap. An ECG is simultaneously recorded by a three-electrode ECG circuit with three electrodes attached to a wrist and the left and right ankles. The device and ECG circuit is connected to a computer that performs the signal processing and waveform display.

As shown in FIG. 14, panel B, the device can be disposed in various positions on the subject's chest, resulting in differences in the efficacy and output. The device can also be put against the back of the human subject to record data.

The human subject is in a comfortable and warm environment and is relaxed. The subject can stand, sit, walk or lie down on a bed. The device can be positioned to contact the skin or can be placed outside the subject's clothing. In the clothed setting, the device can be placed tightly against chest of the subject.

Example 5

Representative Subject Measurements

Figure 15:
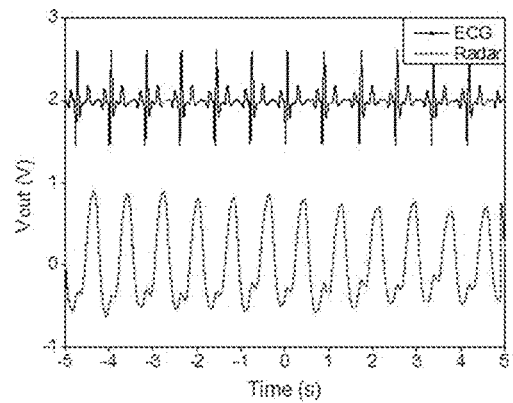
FIG. 15 is paired ECGs and measurements with a representative device of the invention in human subjects.
Figure 15:
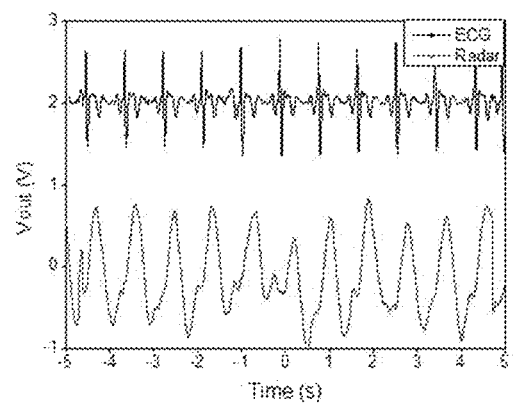
Figure 15:
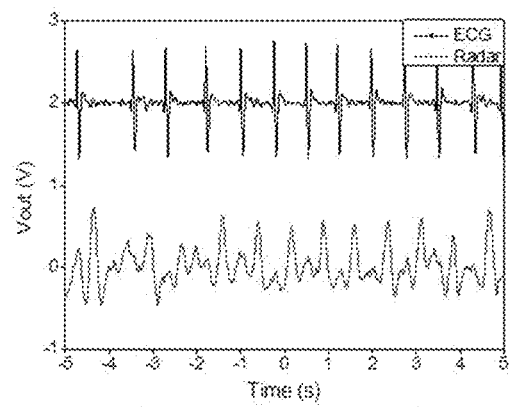

Three subjects were monitored using a device of the invention. All data were taken with the subjects in a held breath state. FIG. 15, panel A shows the ECG signal on the top graph and the radar signal on the bottom graph detected in a healthy young man. FIG. 15, panel B shows the ECG signal on the top graph and the radar signal on the bottom graph detected in a healthy elderly man. FIG. 15, panel C shows the ECG signal on the top graph and the radar signal on the bottom graph detected in an elderly man with an irregular heartbeat, who is in atrial fibrillation. In panels A and B, the small first pulse was generated by the motion of the atrium and the larger second pulse was generated by the motion of the ventricles. In panels A and B, the radar signals from the invention correlated with the ECG signals and were in the same periodicity as the ECG signals. In panel C, the radar signal correlated with the ECG signal but showed little evidence of atrial motion.

Example 6

Subject Measurements while Breathing

Figure 16:
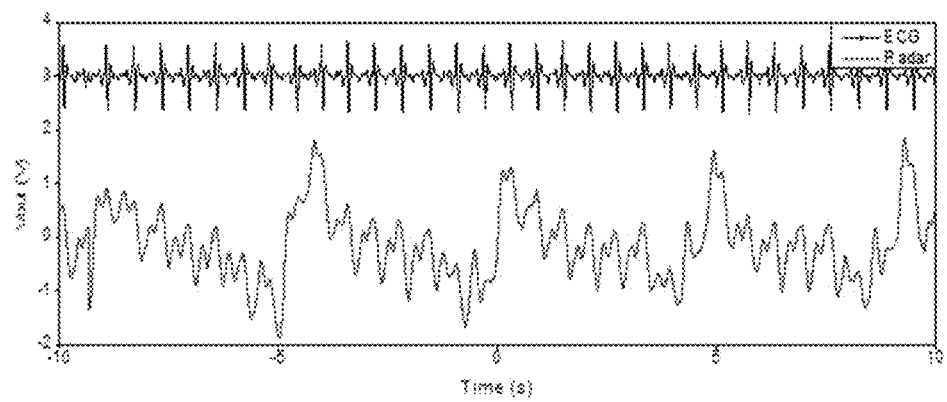
FIG. 16 is a paired ECG and measurement with a representative device of the invention in a human subject.

FIG. 16 shows the ECG signal on the top graph and the radar signal on the bottom graph detected in the healthy young man in Example 5 while breathing. The additional low frequency signal superimposed on the radar heart motion signal represents the motion of the chest cavity as a result of breathing.

Example 7

Subject Measurements at Different Chest Positions

Figure 17:
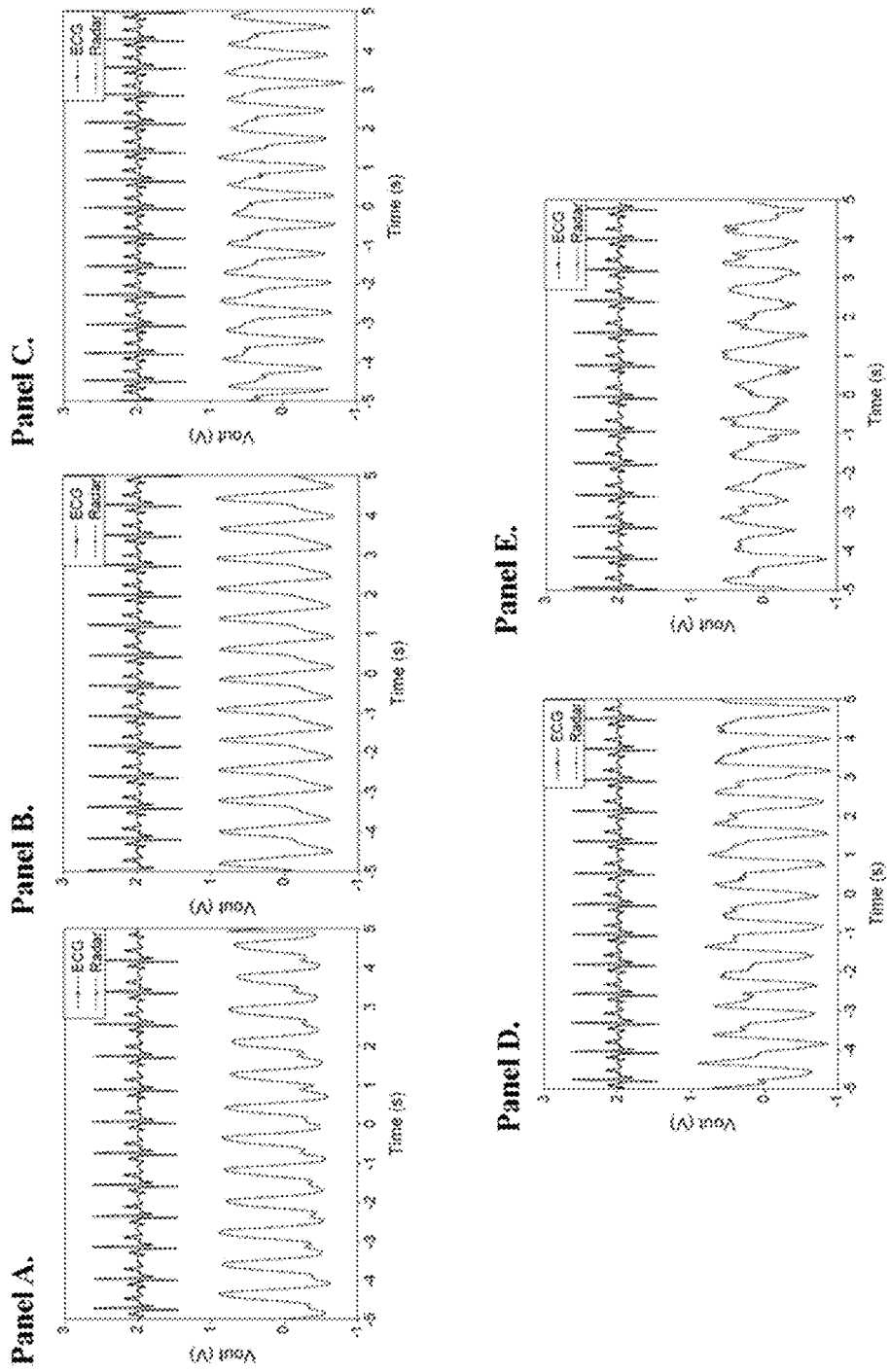
FIG. 17 is paired ECGs and measurements with a representative device of the invention in a human subject.

As described in Example 4, FIG. 17 shows the ECG signal on the top graph and the radar signal on the bottom graph when a representative device of the invention was positioned at different locations on the chest of the healthy young man from Example 5. Panel A illustrates the ECG and radar signals measured at the center of the chest. Panel B illustrates the ECG and radar signals measured above the center of the chest Panel C illustrates the ECG and radar signals measured below the center of the chest. Panel D illustrates the ECG and radar signals measured left of the center of the chest. Panel E illustrates the ECG and radar signals measured right of the center of the chest. These graphs show that positioning the device at various locations on the chest allowed views of different portions of the heart. Viewing different portions of the heart can assist evaluation of various heart abnormalities.

Example 8

Subject Measurements from the Back

Figure 18:
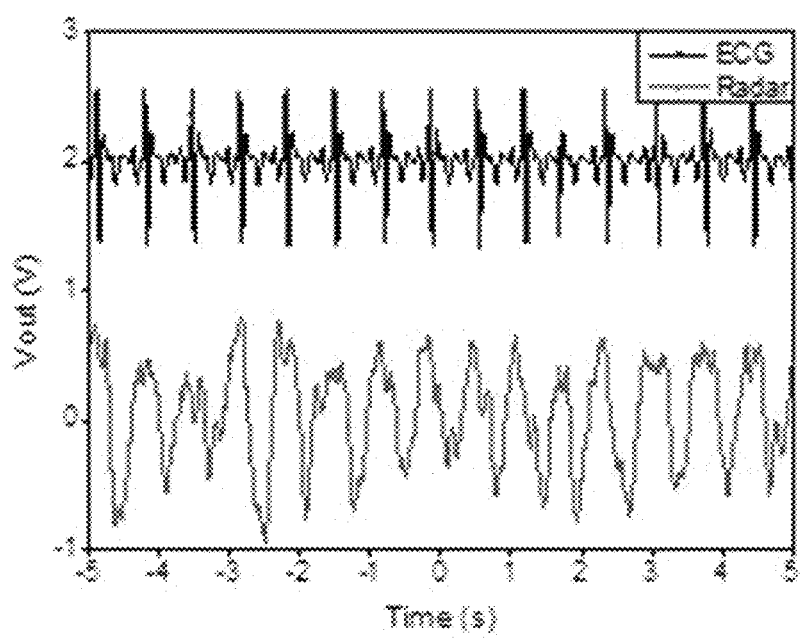
FIG. 18 is a paired ECG and measurement with a representative device of the invention in a human subject.

FIG. 18 shows the ECG signal on the top graph and the radar signal on the bottom graph obtained when a device of the invention was positioned on the back of the healthy young man from Example 5. These data represent measurements of atrial motion by positioning the device on the back of the subject.

Example 9

Subject Measurements at a Distance

Figure 21:
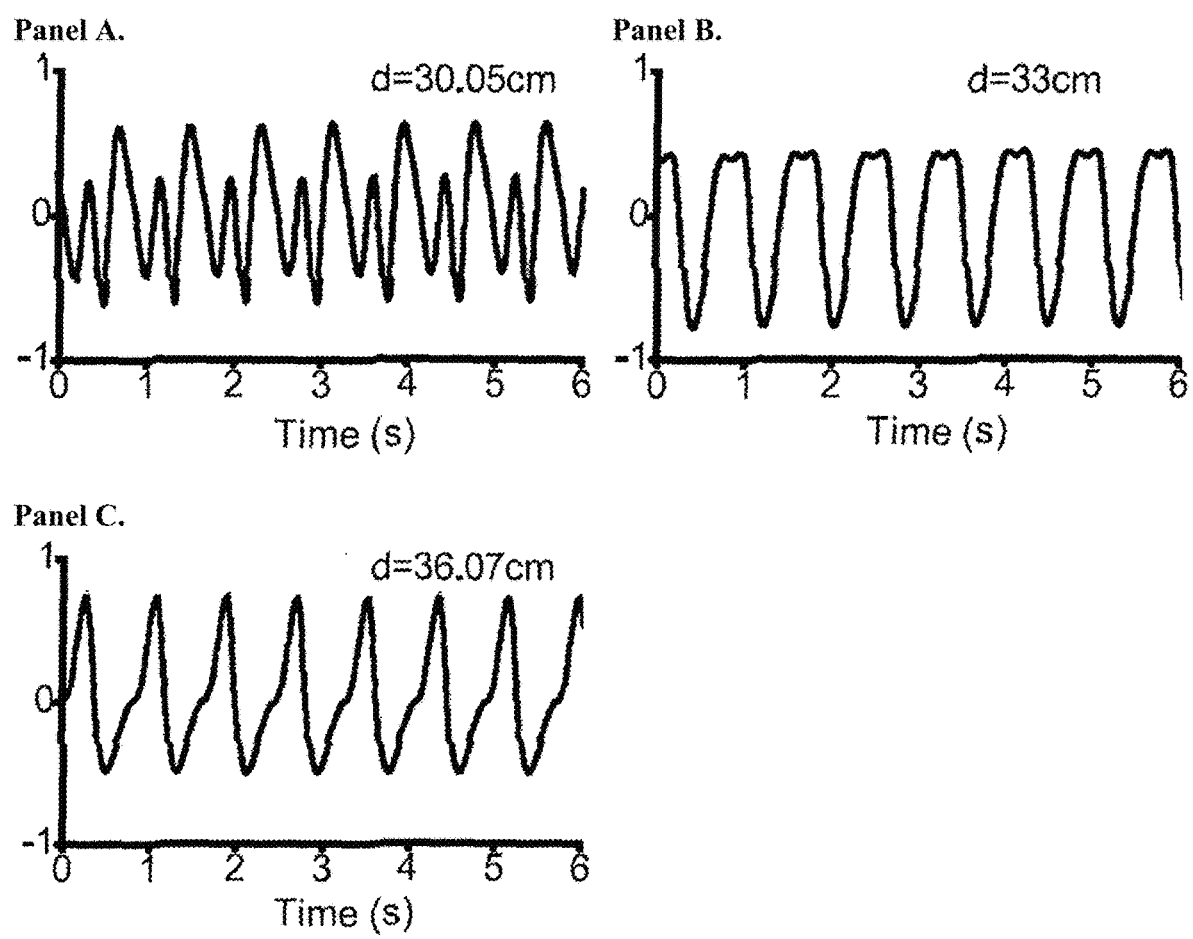
FIG. 21 depicts measured waveforms from the representative radar device.

FIG. 21 shows three measurements taken from a healthy male subject at different distances. All of these data were taken with the subject in a held breath state. These data represent measurements of atrial motion by positioning an embodiment of the invention at a distance from the subject.

Example 10

Improving Data Quality by Quadrature Demodulation

Figure 19:
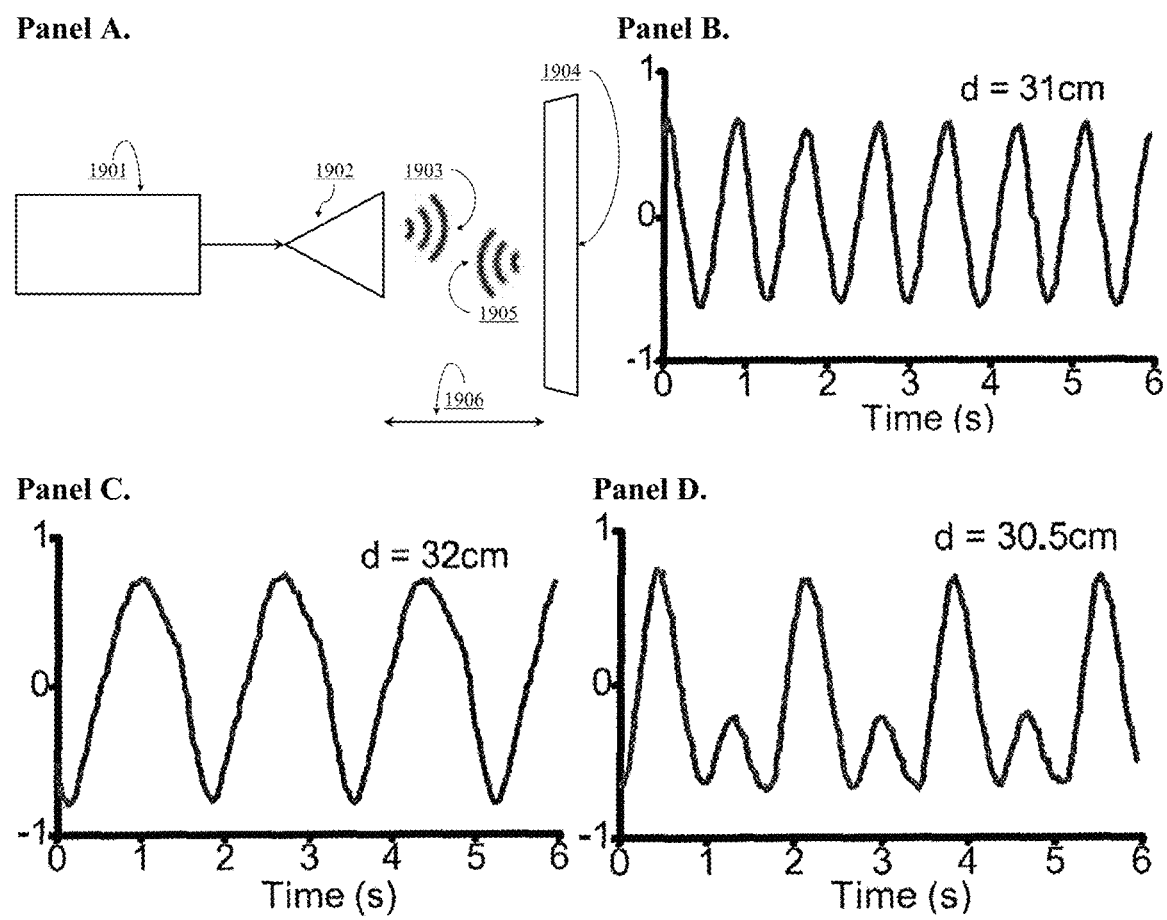
FIG. 19 depicts a representative device of the invention and measured waveforms from the representative radar device.

FIG. 19, panel A illustrates an embodiment of a device to determine the motion of the heart of a subject. The radar system 1901 connected to an antenna 1902 propagates a transmitted waveform 1903 towards a target 1904, for example, a heart of a subject. A reflected waveform 1905 is then received by the antenna 1902. The distance between the antenna 1902 and the target 1904 is defined by the function 1906 d−x(t), where d is a constant distance between the antenna 1902 and the target 1904 and x(t) is the motion function of the target 1904, for example, the original motion of the heart of the subject. Panels B-D represent measured waveforms at three different distances between the antenna 1902 and target 1904.

The radar system 1901 transmits a cosine signal written as $$T(t) = A \cdot \cos(2\pi f t);$$

where A is the amplitude of the transmitted waveform 1903, f is the frequency of transmitted waveform 1903, and t is time.

The reflected signal is written as $$R(t) = B \cdot \cos\left(2\pi f t - \frac{4\pi d}{\lambda} - \frac{4\pi \cdot x(t)}{\lambda}\right);$$

where B is the amplitude of the reflected waveform 1905 and lambda is the wavelength of reflected waveform 1905.

After demodulation, two output signals can exist. One is called an in-phase signal (I) and the other is called a quadrature signal (Q). The in-phase signal is written as $$I(t) = C \cdot \cos\left(\frac{4\pi d}{\lambda} + \frac{4\pi \cdot x(t)}{\lambda}\right);$$

and the quadrature signal is written as $$Q(t) = C \cdot \sin\left(\frac{4\pi d}{\lambda} + \frac{4\pi \cdot x(t)}{\lambda}\right);$$

where C is the amplitude of the signal.

By dividing Q(t) by I(t), the signal ratio Y is obtained, which is written as $$Y(t) = \tan\left(\frac{4\pi d}{\lambda} + \frac{4\pi \cdot x(t)}{\lambda}\right).$$

Thus, solution is possible for the motion function of the target in terms of the signal ratio, with x(t) written as $$x(t) = \frac{\lambda}{4\pi} \cdot \tan^{-1}(Y(t)) - d.$$

Quadrature demodulation as described herein can allow for precise calculation of the motion function of the target 1904, since motion of the target 1904 is quite small compared with the wavelength of the reflected waveform 1905.

Example 11

Continuous Monitoring to Inform Decision-Making on Interventions

Figure 20:
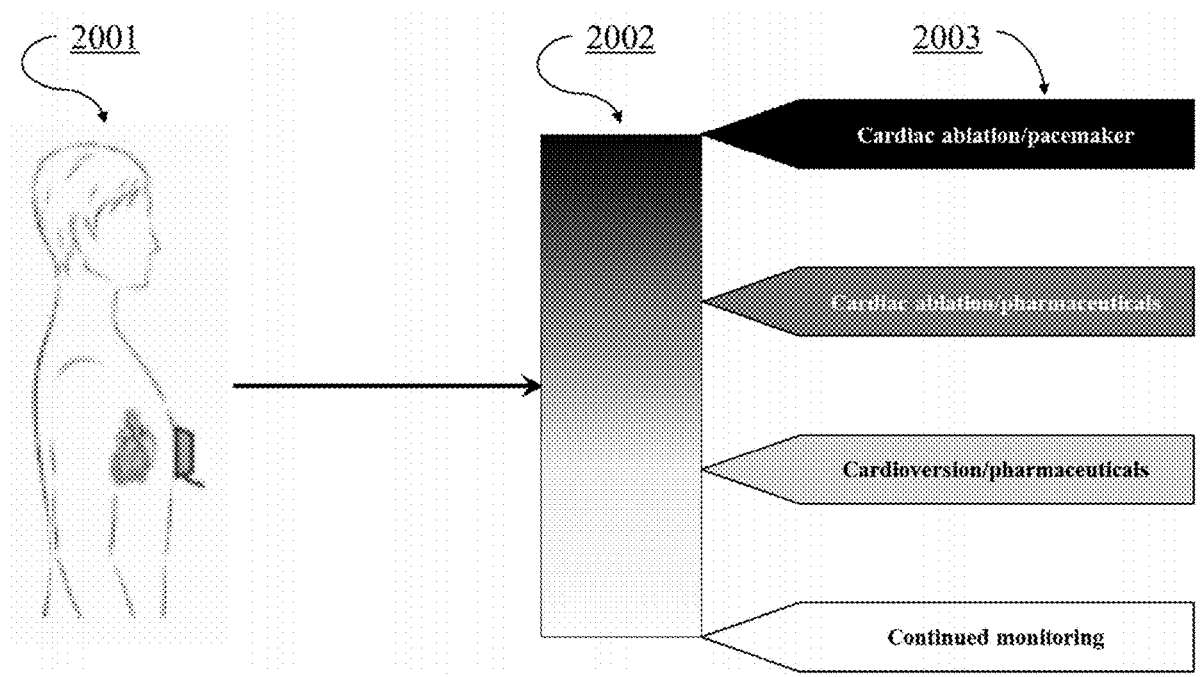
FIG. 20 illustrates a method of monitoring that can be used in connection with example embodiments of the present invention.

FIG. 20 illustrates an embodiment of the method of continuous monitoring described in the invention. For example, a subject can wear a device continuously for long-term monitoring 2001 to determine the percentage of cardiac arrhythmic time 2002. These data are recorded and stored over long periods of time, for example, hours, days, weeks, or months. Signal recognition software detects and highlights important events for review by a health care provider. The health care provider uses the percentage of cardiac arrhythmic time 2002 to determine the appropriate medical intervention 2003. Non-limiting examples of medical interventions include continued monitoring; cardioversion with or without specific pharmaceuticals; cardiac ablation with or without specific pharmaceuticals; and cardiac ablation with or without introduction of a pacemaker.

EMBODIMENTS

The following non-limiting embodiments provide illustrative examples of the invention, but do not limit the scope of the invention.

Embodiment 1

A method of detecting an irregular heartbeat in a subject, the method comprising: a) transmitting a wavelength of electromagnetic radiation to the heart of the subject; b) detecting an electromagnetic signal reflected off the heart of the subject; and c) determining based on the electromagnetic signal reflected off the heart of the subject whether the subject has an irregular heartbeat.

Embodiment 2

The method of Embodiment 1, wherein the subject is undergoing an intervention for the irregular heartbeat, the method further comprising determining based on the electromagnetic signal reflected off the heart of the subject whether the intervention for the irregular heartbeat has modulated the irregular heartbeat.

Embodiment 3

The method of Embodiment 1, wherein the subject is undergoing an intervention for a non-irregular heartbeat condition, the method further comprising determining based on the electromagnetic signal reflected off the heart of the subject whether the intervention for the non-irregular heartbeat condition has induced the irregular heartbeat.

Embodiment 4

The method of any one of Embodiments 1-3, wherein the determination whether the subject has an irregular heartbeat is determined by an analysis of a movement of a portion of the heart.

Embodiment 5

The method of any one of Embodiments 1-4, further comprising attaching a source of electromagnetic radiation to the subject's body.

Embodiment 6

The method of Embodiment 5, wherein the source of electromagnetic radiation is attached to the subject's body in proximity to the subject's heart.

Embodiment 7

The method of Embodiment 5, wherein the source of electromagnetic radiation is attached to the subject's chest.

Embodiment 8

The method of Embodiment 5, wherein the source of electromagnetic radiation is attached to the subject's back.

Embodiment 9

The method of any one of Embodiments 1-8, wherein the subject is in a held-breath state.

Embodiment 10

The method of any one of Embodiments 1-9, wherein the wavelength of electromagnetic radiation transmitted to the heart of the subject is a radio wave.

Embodiment 11

The method of any one of Embodiments 1-10, wherein the irregular heartbeat is associated with atrial fibrillation.

Embodiment 12

The method of any one of Embodiments 1-10, wherein the irregular heartbeat is associated with atrial flutter.

Embodiment 13

The method of any one of Embodiments 1-10, wherein the irregular heartbeat is associated with ventricular fibrillation.

Embodiment 14

The method of any one of Embodiments 1-10, wherein the irregular heartbeat is associated with ventricular flutter.

Embodiment 15

The method of any one of Embodiments 1-10, wherein the irregular heartbeat is associated with cardiac arrhythmia.

Embodiment 16

The method of any one of Embodiments 1-15, wherein the subject is human.

Embodiment 17

A method comprising: a) receiving by a computer system data associated with an electromagnetic signal reflected off a heart of a subject; b) comparing by a processor of the computer system the data associated with the electromagnetic signal reflected off the heart of the subject to a reference; c) determining based on the comparison of the data associated with the electromagnetic signal reflected off the heart of the subject to the reference whether the subject has an irregular heartbeat; and d) outputting a result of the determination.

Embodiment 18

The method of Embodiment 17, wherein the subject is undergoing an intervention for the irregular heartbeat, the method further comprising determining based on the electromagnetic signal reflected off the heart of the subject whether the intervention for the irregular heartbeat has modulated the irregular heartbeat.

Embodiment 19

The method of Embodiment 17, wherein the subject is undergoing an intervention for a non-irregular heartbeat condition, the method further comprising determining based on the electromagnetic signal reflected off the heart of the subject whether the intervention for the non-irregular heartbeat condition has induced the irregular heartbeat.

Embodiment 20

The method of any one of Embodiments 17-19, wherein the determination that the subject has an irregular heartbeat is determined by an analysis of a movement of a portion of the heart.

Embodiment 21

The method of any one of Embodiments 17-20, wherein the irregular heartbeat is associated with atrial fibrillation.

Embodiment 22

The method of any one of Embodiments 17-20, wherein the irregular heartbeat is associated with atrial flutter.

Embodiment 23

The method of any one of Embodiments 17-20, wherein the irregular heartbeat is associated with ventricular fibrillation.

Embodiment 24

The method of any one of Embodiments 17-20, wherein the irregular heartbeat is associated with ventricular flutter.

Embodiment 25

The method of any one of Embodiments 17-20, wherein the irregular heartbeat is associated with cardiac arrhythmia.

Embodiment 26

The method of any one of Embodiments 17-25, wherein the subject is human.

Embodiment 27

A device comprising: a) an antenna configured to transmit electromagnetic radiation into a thoracic cavity of a subject; b) a receiver configured to detect an electromagnetic signal reflected off the subject's heart; and c) a processor configured to identify an irregular heartbeat in the subject based on the detected electromagnetic signal reflected off the subject's heart.

Embodiment 28

The device of Embodiment 27, wherein the antenna configured to transmit the electromagnetic radiation into the thoracic cavity of the subject, the receiver configured to detect the electromagnetic signal reflected off the subject's heart, and the processor configured to identify the irregular heartbeat in the subject based on the detected electromagnetic signal reflected off the subject's heart, are contained in a common housing.

Embodiment 29

The device of any one of Embodiments 27-28, further comprising a circuit configured to generate a signal suitable for transmission into the thoracic cavity of the subject by the antenna.

Embodiment 30

The device of any one of Embodiments 27-29, wherein the processor is configured to detect the irregular heartbeat in a subject by measuring time intervals among signals received after reflection off the subject's heart.

Embodiment 31

The device of any one of Embodiments 27-30, wherein the antenna is configured to transmit electromagnetic radiation that is a radio wave.

Embodiment 32

The device of any one of Embodiments 27-31, wherein the device is configured to be attached to the subject in proximity to the subject's heart.

Embodiment 33

The device of any one of Embodiments 27-32, wherein the device is configured to be attached to the subject on the subject's chest.

Embodiment 34

The device of any one of Embodiments 27-32, wherein the device is configured to be attached to the subject on the subject's back.

Embodiment 35

The device of any one of Embodiments 24-34, wherein the processor is configured to identify an irregular heartbeat associated with atrial fibrillation.

Embodiment 36

The device of any one of Embodiments 24-34, wherein the processor is configured to identify an irregular heartbeat associated with atrial flutter.

Embodiment 37

The device of any one of Embodiments 24-34, wherein the processor is configured to identify an irregular heartbeat associated with ventricular fibrillation.

Embodiment 38

The device of any one of Embodiments 24-34, wherein the processor is configured to identify an irregular heartbeat associated with ventricular flutter.

Embodiment 39

The device of any one of Embodiments 24-34, wherein the processor is configured to identify an irregular heartbeat associated with cardiac arrhythmia.

Embodiment 40

A device comprising: a) an antenna configured to transmit electromagnetic radiation into a thoracic cavity of a subject; b) a receiver configured to detect an electromagnetic signal reflected off the subject's heart; and c) a transmitter configured to transmit data associated with the received electromagnetic signal reflected off the subject's heart.

Embodiment 41

The device of Embodiment 40, wherein the antenna configured to transmit the electromagnetic radiation into the thoracic cavity of the subject, the receiver configured to detect the electromagnetic signal reflected off the subject's heart, and the transmitter configured to transmit data associated with the received electromagnetic signal reflected off the subject's heart, are contained in a common housing.

Embodiment 42

The device of any one of Embodiments 40-41, further comprising a circuit configured to generate a signal suitable for transmission into the thoracic cavity of the subject by the antenna.

Embodiment 43

The device of any one of Embodiments 40-42, wherein the transmitter is configured to transmit wirelessly to a remote processor.

Embodiment 44

The device of any one of Embodiments 40-43, wherein the antenna is configured to transmit electromagnetic radiation that is a radio wave.

Embodiment 45

The device of any one of Embodiments 40-44, wherein the device is configured to be attached to the subject in proximity to the subject's heart.

Embodiment 46

The device of any one of Embodiments 40-45, wherein the device is configured to be attached to the subject on the subject's chest.

Embodiment 47

The device of any one of Embodiments 40-45, wherein the device is configured to be attached to the subject on the subject's back.

Embodiment 48

A method comprising: a) administering to a subject having an irregular heartbeat an intervention for the irregular heartbeat; b) monitoring the subject with a radar device; and c) determining based on the monitoring whether the intervention for the irregular heartbeat modulates the irregular heartbeat in the subject.

Embodiment 49

The method of Embodiment 48, wherein the radar device monitors a movement of a portion of the subject's heart.

Embodiment 50

The method of any one of Embodiments 48-49, wherein the processor is configured to identify an irregular heartbeat associated with atrial fibrillation.

Embodiment 51

The method of any one of Embodiments 48-49, wherein the processor is configured to identify an irregular heartbeat associated with atrial flutter.

Embodiment 52

The method of any one of Embodiments 48-49, wherein the processor is configured to identify an irregular heartbeat associated with ventricular fibrillation.

Embodiment 53

The method of any one of Embodiments 48-49, wherein the processor is configured to identify an irregular heartbeat associated with ventricular flutter.

Embodiment 54

The method of any one of Embodiments 48-49, wherein the processor is configured to identify an irregular heartbeat associated with cardiac arrhythmia.

Embodiment 55

A method comprising: a) administering to a subject an intervention; b) monitoring the subject with a radar device; and c) determining based on the monitoring whether the intervention induces an irregular heartbeat in the subject.

Embodiment 56

The method of Embodiment 55, wherein the radar device monitors a movement of a portion of the subject's heart.

Embodiment 57

The method of any one of Embodiments 55-56, wherein the processor is configured to identify an irregular heartbeat associated with atrial fibrillation.

Embodiment 58

The method of any one of Embodiments 55-56, wherein the processor is configured to identify an irregular heartbeat associated with atrial flutter.

Embodiment 59

The method of any one of Embodiments 55-56, wherein the processor is configured to identify an irregular heartbeat associated with ventricular fibrillation.

Embodiment 60

The method of any one of Embodiments 55-56, wherein the processor is configured to identify an irregular heartbeat associated with ventricular flutter.

Embodiment 61

The method of any one of Embodiments 55-56, wherein the processor is configured to identify an irregular heartbeat associated with cardiac arrhythmia.

Embodiment 62

The method of any one of Embodiments 55-61, wherein the subject has a non-irregular heartbeat condition, and the intervention is for the non-irregular heartbeat condition.

Embodiment 63

A method comprising: a) transmitting a wavelength of electromagnetic radiation to the heart of the subject; b) detecting an electromagnetic signal reflected off the heart of the subject; and c) determining based on the electromagnetic signal reflected off the heart of the subject a change in volume of the heart of the subject.

Embodiment 64

The method of Embodiment 63, further comprising determining a volume of blood output from the heart of the subject based on the change in volume of the heart of the subject.

Embodiment 65

The method of any one of Embodiments 63-64, wherein the change in volume of the heart of the subject is determined within a single chamber of the heart of the subject.

What is claimed is:

1. A method of detecting an irregular heartbeat of a heart in a subject, the method comprising:
   a) positioning directly in front of a sternum of the subject a transmitter-containing device, wherein the device is in contact with skin or clothing of the subject, wherein the transmitter-containing device comprises a transmitter, a circuit board, an antenna, and a receiver in a common housing;
   b) transmitting by the transmitter of the transmitter-containing device electromagnetic radiation through the antenna to the heart of the subject, wherein the circuit board generates the electromagnetic radiation transmitted by the antenna, wherein the electromagnetic radiation propagates to the heart of the subject and is reflected off the heart of the subject;
   c) detecting by the receiver a wavelength of the electromagnetic radiation reflected off the heart of the subject; and
   d) determining by a processor based on the wavelength of the electromagnetic radiation reflected off the heart of the subject whether the subject has the irregular heartbeat, wherein the determining whether the subject has the irregular heartbeat is by detecting a relative position of a portion of the heart of the subject as compared to other portions of the heart, wherein the electromagnetic radiation transmitted to the heart of the subject is a radio wave.

2. The method of claim 1, wherein the subject is undergoing an intervention for the irregular heartbeat, the method further comprising determining based on the wavelength of the electromagnetic radiation reflected off the heart of the subject whether the intervention for the irregular heartbeat has modulated the irregular heartbeat.

3. The method of claim 1, wherein the subject is undergoing an intervention for a non-irregular heartbeat condition, the method further comprising determining based on the wavelength of the electromagnetic radiation reflected off the heart of the subject whether the intervention for the non-irregular heartbeat condition has induced the irregular heartbeat.

4. The method of claim 1, wherein the determination whether the subject has an irregular heartbeat is determined by an analysis of a movement of a portion of the heart.

5. The method of claim 1, wherein the subject is in a held-breath state.

6. The method of claim 1, wherein the irregular heartbeat is associated with atrial fibrillation.

7. The method of claim 1, wherein the irregular heartbeat is associated with atrial flutter.

8. The method of claim 1, wherein the irregular heartbeat is associated with ventricular fibrillation.

9. The method of claim 1, wherein the irregular heartbeat is associated with ventricular flutter.

10. The method of claim 1, wherein the irregular heartbeat is associated with cardiac arrhythmia.

11. The method of claim 1, wherein the subject is human.

12. The method of claim 1, wherein the determination whether the subject has an irregular heartbeat is determined by an analysis of a movement of an atrium of the heart.

13. The method of claim 1, wherein the determination whether the subject has an irregular heartbeat is determined by an analysis of a movement of a ventricle of the heart.

14. The method of claim 1, wherein the determination whether the subject has an irregular heartbeat is determined by an analysis of a change in a dimension of the heart.

15. The method of claim 1, wherein the determination whether the subject has an irregular heartbeat is determined by an analysis of a velocity of a muscle of the heart.

16. The method of claim 1, wherein the transmitter-containing device is attached to the subject by a strap.

17. The method of claim 1, wherein the irregular heartbeat is associated with supraventricular tachycardia.

18. The method of claim 1, wherein the irregular heartbeat is associated with multifocal atrial tachycardia.

19. The method of claim 1, wherein the irregular heartbeat is associated with Wolff-Parkinson-White syndrome.

20. The method of claim 1, wherein the irregular heartbeat is associated with premature atrial contraction.

21. The method of claim 1, wherein the irregular heartbeat is associated with premature ventricular contraction.

22. The method of claim 1, wherein the irregular heartbeat is associated with sick sinus syndrome.

23. The method of claim 1, wherein the irregular heartbeat is associated with bradycardia.

24. The method of claim 1, wherein positioning of the transmitter-containing device is to the center of a chest of the subject.

25. The method of claim 1, wherein the receiver is a Doppler radar sensor.

26. The method of claim 25, wherein the Doppler radar sensor is a continuous wave Doppler radar sensor.

27. The method of claim 1, wherein the determining whether the subject has the irregular heartbeat is by detecting an intensity of a heartbeat of the subject.

28. The method of claim 1, wherein the determining whether the subject has the irregular heartbeat is by detecting a percentage of time the subject has irregular heartbeat.

29. The method of claim 1, wherein the determining whether the subject has the irregular heartbeat is by detecting a percentage of cardiac arrhythmia time in the subject.

30. The method of claim 1, wherein the electromagnetic radiation reflected off the heart of the subject indicates a relative position of a portion of the heart of the subject.

31. The method of claim 1, wherein the electromagnetic radiation reflected off the heart of the subject indicates a motion of the heart of the subject.

32. The method of claim 1, wherein the determining whether the subject has the irregular heartbeat is by detecting a motion of the relative position of the portion of the heart of the subject as compared to other portions of the heart.

* * * * *